United States Patent
Roth et al.

(10) Patent No.: US 8,252,081 B2
(45) Date of Patent: *Aug. 28, 2012

(54) WATER DISSIPATION DEVICE AND METHOD

(75) Inventors: Gary James Roth, Wake Forest, NC (US); Daniel Patrick Dwyer, Raleigh, NC (US); Jorge Jimenez Perez, Raleigh, NC (US); Jarred Gabriel DeVille, Wake Forest, NC (US); Jason David Foushee, Durham, NC (US)

(73) Assignee: Teleflex Medical Incorporated, Research Triangle Park, NC (US)

( * ) Notice: Subject to any disclaimer, the term of this patent is extended or adjusted under 35 U.S.C. 154(b) by 431 days.

This patent is subject to a terminal disclaimer.

(21) Appl. No.: 12/539,088

(22) Filed: Aug. 11, 2009

(65) Prior Publication Data

US 2010/0012127 A1     Jan. 21, 2010

Related U.S. Application Data

(63) Continuation-in-part of application No. 12/145,902, filed on Jun. 25, 2008, now Pat. No. 8,105,410, which is a continuation-in-part of application No. 11/826,597, filed on Jul. 17, 2007.

(51) Int. Cl.
*B01D 46/00* (2006.01)
(52) U.S. Cl. ............... 55/498; 55/309; 55/312; 55/314; 55/DIG. 33; 55/DIG. 34
(58) Field of Classification Search .............. 55/309, 55/312, 314, DIG. 33, DIG. 34; 95/46, 52; 36/4, 108, 124, 125, 150; 128/205.29, 205.27, 128/203.16, 202.13
See application file for complete search history.

(56) References Cited

U.S. PATENT DOCUMENTS

| | | | |
|---|---|---|---|
| 3,747,598 A | 7/1973 | Cowans | |
| 4,172,709 A | 10/1979 | Kippel et al. | |
| 4,200,094 A | 4/1980 | Gedeon et al. | |
| 4,232,667 A | 11/1980 | Chalon et al. | |

(Continued)

FOREIGN PATENT DOCUMENTS

FR    2692153 A1    12/1993

(Continued)

OTHER PUBLICATIONS

Extended European Search Report of EP 08 77 2247 dated Jun. 18, 2012.

*Primary Examiner* — Jason M Greene
*Assistant Examiner* — Karla Hawkins
(74) *Attorney, Agent, or Firm* — Baker & Hostetler LLP

(57) ABSTRACT

A water dissipation device for removing water vapor or moisture from a breathing circuit is provided, including an upper lid portion, an entry port and an exit port. An outer cover structure extends from the upper lid portion to define an enclosed volume. An inner frame extends from the upper lid portion inside the outer cover structure. The outer cover structure includes a first layer of water or moisture wicking material and a second layer of water vapor breathable medium, and has an inner surface area bounding an inner flow space such that water vapor or moisture can permeate from the inner flow space through the outer cover structure out of device. The device can include an inner cup structure extending from the upper lid portion into the enclosed volume to displace the enclosed volume and define and bound a portion of the inner flow space and compressible volume therein.

35 Claims, 24 Drawing Sheets

U.S. PATENT DOCUMENTS

| | | | |
|---|---|---|---|
| 4,548,626 A | 10/1985 | Ackley et al. | |
| 4,771,770 A | 9/1988 | Artemenko et al. | |
| 5,035,236 A | 7/1991 | Kanegaonkar | |
| 5,195,527 A | 3/1993 | Hicks | |
| 5,230,727 A | 7/1993 | Pound et al. | |
| 5,460,172 A | 10/1995 | Eckerbom et al. | |
| 5,505,768 A | 4/1996 | Altadonna | |
| 6,415,788 B1 | 7/2002 | Clawson et al. | |
| 6,550,476 B1 | 4/2003 | Ryder | |
| 6,792,946 B1 | 9/2004 | Waldo, Jr. et al. | |
| 6,976,488 B2 | 12/2005 | Halperin | |
| 7,140,366 B2 | 11/2006 | Smith et al. | |
| 2001/0054422 A1 | 12/2001 | Smith et al. | |
| 2002/0002976 A1 | 1/2002 | Smith et al. | |
| 2004/0123974 A1 | 7/2004 | Marler et al. | |

FOREIGN PATENT DOCUMENTS

| | | |
|---|---|---|
| GB | 2267661 A | 12/1996 |
| WO | WO 99/60954 A1 | 12/1999 |
| WO | WO 2005/047797 A2 | 5/2005 |

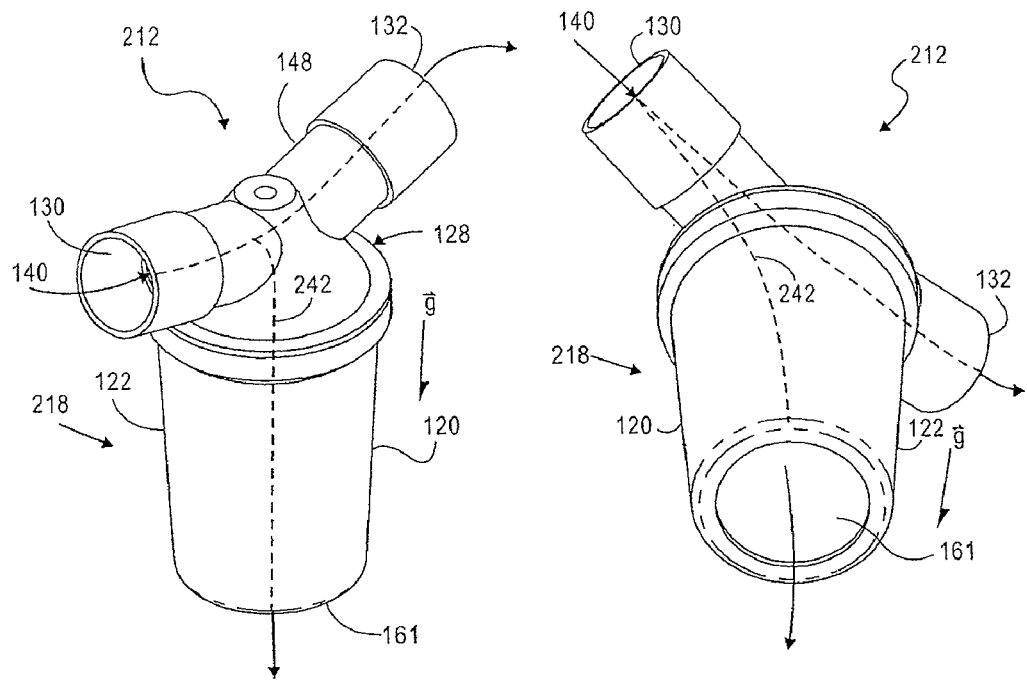
FIG. 9
FIG. 10
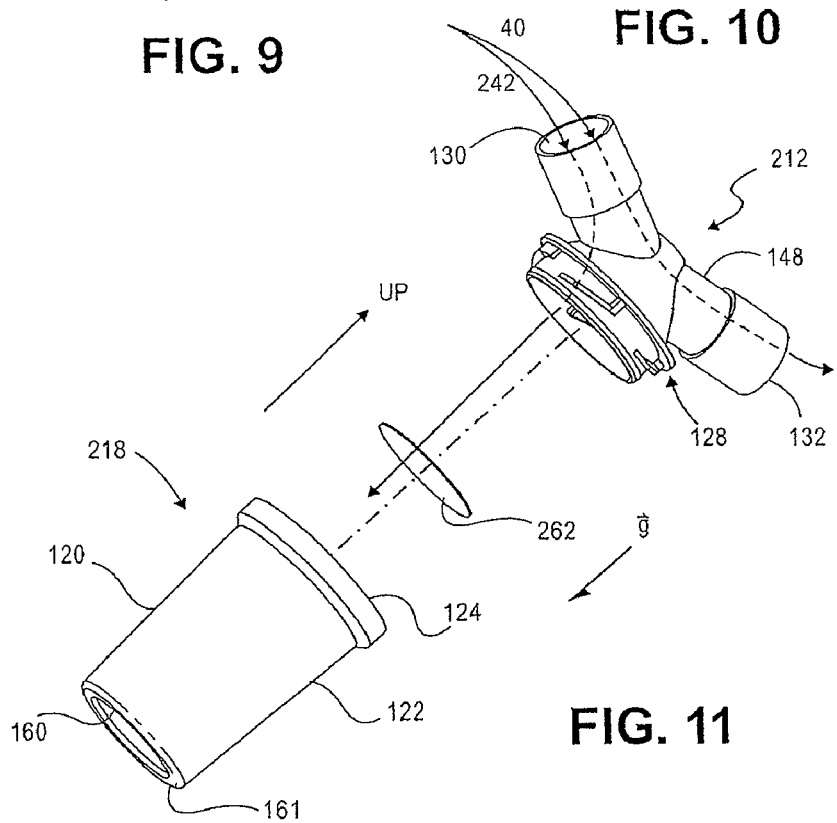
FIG. 11

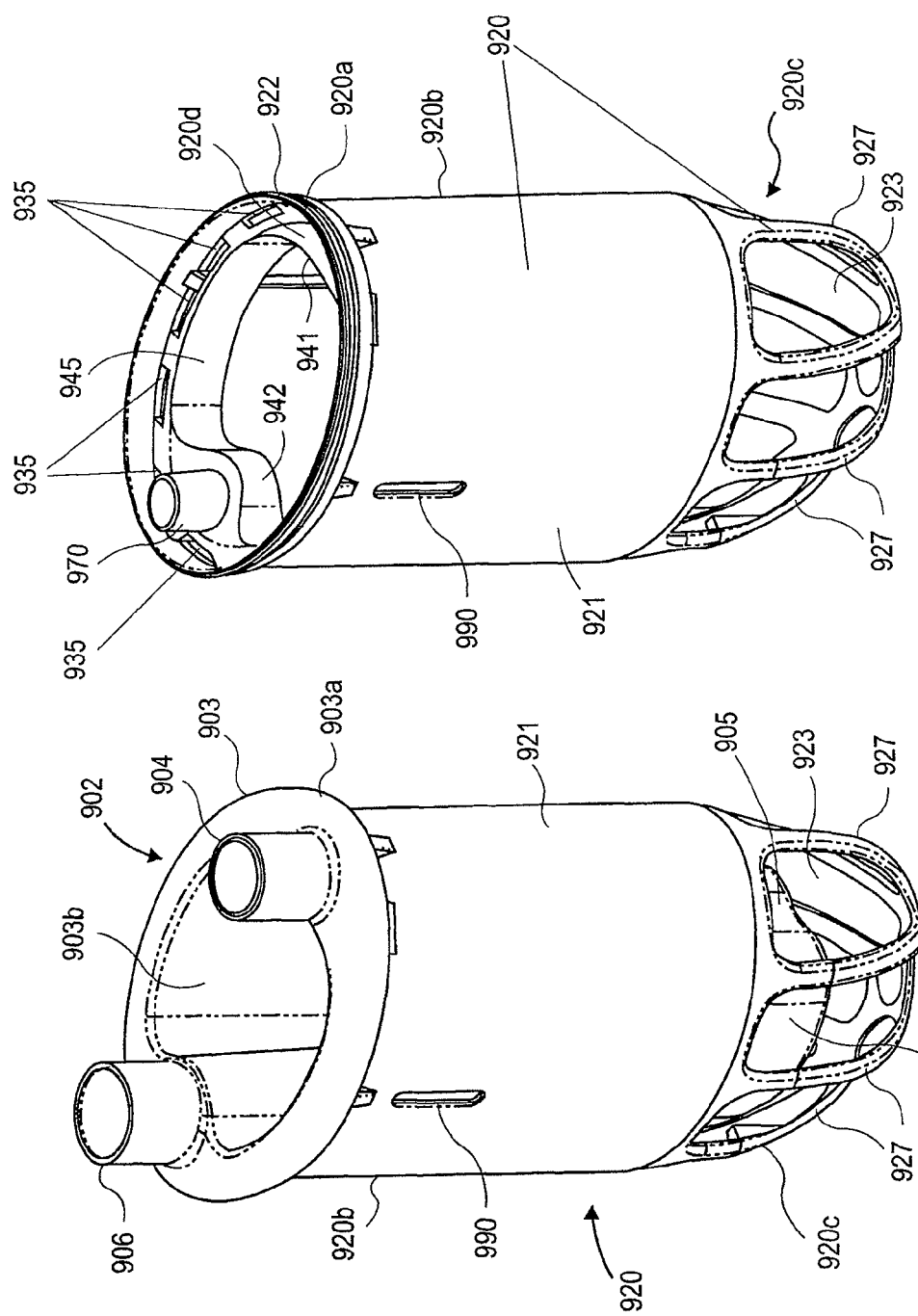

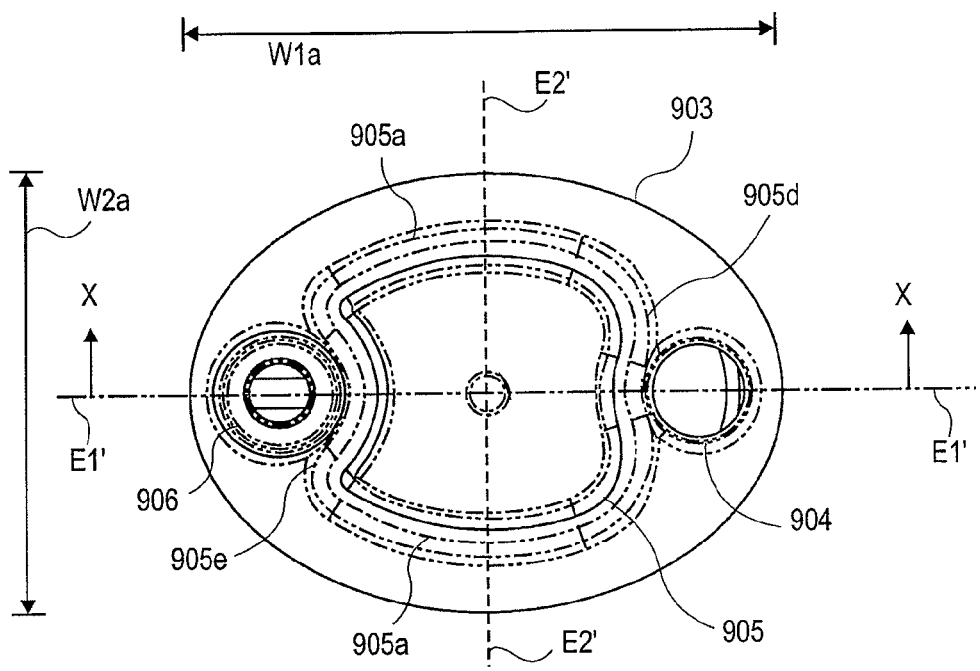
FIG. 29
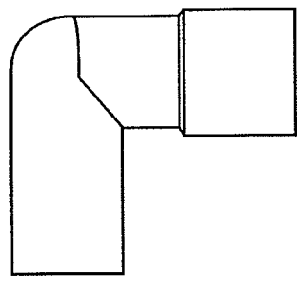 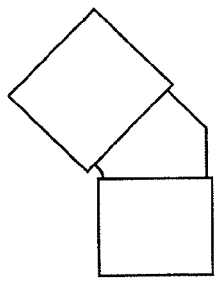 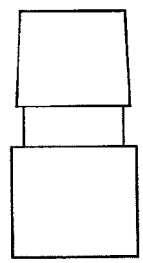
FIG. 32A    FIG. 32B    FIG. 32C

WATER DISSIPATION DEVICE AND METHOD

CROSS-REFERENCE TO RELATED APPLICATIONS

The present application claims priority to and is a continuation-in-part of U.S. application Ser. No. 12/145,902, filed Jun. 25, 2008, now pending, which is a continuation-in-part of U.S. application Ser. No. 11/826,597, filed Jul. 17, 2007, now pending, the entire contents of which are incorporated herein by reference.

FIELD OF THE INVENTION

The present invention relates generally to a medical device. More particularly, the present invention is related to a water dissipation device for placement with a breathing circuit.

BACKGROUND

A breathing circuit delivers medical gas to a patient under pressure in a prescribed volume and breathing rate. The medical gas is often humidified by a humidifier located at or near the ventilator or respirator. The optimum respiratory circuit delivers 100% RH medical gases @ 35 to 39 degrees C. to the patient while reducing the amount of humidity and subsequent condensate delivered back to the ventilator through the expiratory limb. Therefore, the humidified gas has to travel through all or most of the tubing and has time to cool. Cooling of the gas leads to rainout or condensation in the breathing tube and collection of water within the breathing circuit.

Several solutions to the problem of rainout have been developed. One such solution is a heating wire provided along the length of the tube. The wire may be provided within the interior of the tubing or alternatively may be embedded along the interior of the tubing. The wire heats the humidified gas traveling through the tubing to prevent the gas from cooling, thus preventing the problem of water condensing out of the gas traveling through the breathing circuit. However, the manufacture of such heated wire respiratory circuits can be time consuming and costly.

Another such solution, which eliminates the heated wire, is to provide a water collection device somewhere within the breathing circuit. A water collection apparatus is typically placed in the expiratory limb of the respiratory circuit in front of the ventilator or respirator to collect and manually remove excessive condensation prior to the gases entering the ventilator or respirator. It is known that excessive condensate entering a ventilator or respirator from the expiratory limb of a respiratory circuit can harm the device.

Most frequently, the water collection device is designed to trap the condensed water vapor in a removable container. When the container is removed, a valve can be actuated to create a gas tight seal for the breathing circuit. However, this type of water collection device has to be monitored and manually emptied, causing risk of patient or caregiver infection.

Accordingly, it is desirable to provide an improved apparatus for removing or decreasing water vapor, moisture, or condensate in a breathing circuit. It is further desirable that the improved apparatus for removing water vapor, moisture or condensate from the breathing tube reduce or eliminate the need to heat the exhalation limb of the breathing tube and the need to use currently known water collection or other dissipation devices.

SUMMARY

The foregoing needs are met, to a great extent, by the present invention, wherein an apparatus is provided that in different embodiments provides an improved water dissipation device for placement with a breathing circuit where said water dissipation device will eliminate the need to use a secondary water collection device or manually remove the water condensate and will instead allow for removal of water vapor and/or moisture from the circuit from inside the device out to the surroundings through action of osmosis or permeation or dissipation of such water vapor and/or moisture automatically while the device is coupled to an active breathing circuit. The device includes in one embodiment a composite structure having walls made of different layers including a water or moisture wicking material and water vapor breathable medium, which structure at least partially bounds an inner flow space defined by the device providing an extended area and dwell time for moisture in humidified gases to travel through the composite structure and thereby be removed from the flow in a breathing circuit to which the device is coupled.

In one embodiment of the present invention, a water dissipation device for removing water vapor or moisture from a breathing circuit is provided. The device includes an upper lid portion, an entry port for receiving flow from the breathing circuit, and an exit port for flow exiting the device. An outer cover structure extends from the upper lid portion to define an enclosed volume and a depth between the upper lid portion and a bottom end portion of the device. An inner frame extends from the upper lid portion inside the outer cover structure. The device defines an inner flow space inside the enclosed volume at least for fluid flow from the entry point through the device to the exit port. The outer cover structure includes at least a first layer of water or moisture wicking material and a second layer of water vapor breathable medium over the first layer. The outer cover structure has an inner surface area bounding at least a portion of the inner flow space such that water vapor or moisture can permeate from the inner flow space through the outer cover structure out of device.

In another embodiment, the device can further include an inner cup structure extending from the upper lid portion into the enclosed volume. The inner cup structure can be enclosed by the inner frame and define and bound at least a portion of the inner flow space.

In another embodiment of the present invention, a water dissipation device for removing water vapor or moisture from a breathing circuit is provided. The device includes an upper lid portion, an entry port for receiving flow from the breathing circuit, and an exit port for flow exiting the device. An outer cover structure extends from the upper lid portion to define an enclosed volume and having a depth between the upper lid portion and a bottom end portion of the device. An inner frame extends from the upper lid portion inside the outer cover structure. The device defines an inner flow space inside the enclosed volume at least for fluid flow from the entry point through the device to the exit port. The inner frame includes a substantially cylindrical annular wall portion extending from the upper lid portion for at least one half of the depth of the device or outer cover structure. The outer cover structure includes at least a first layer of water or moisture wicking material and a second layer of water vapor breathable medium over the first layer. The outer cover structure has an inner surface area bounding at least a portion of the inner flow space such that water vapor or moisture can permeate from the inner flow space through the outer cover structure out of device. The outer cover structure narrowly surrounds the annular wall portion of the inner frame to define a narrow annular flow space therebetween, the annular flow space being a portion of the inner flow space and in fluid communication with the entry port.

There has thus been outlined, rather broadly, certain embodiments of the invention in order that the detailed description thereof herein may be better understood, and in order that the present contribution to the art may be better appreciated. There are additional embodiments of the invention that will be described below and which form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 9 is a three-quarter view illustrating another embodiment of the present invention;

FIG. 10 is a bottom view of the embodiment illustrated in FIG. 9;

FIG. 11 is an exploded view of the embodiment illustrated in FIGS. 9 and 10;

FIG. 27 is a view illustrating the water dissipation device of FIG. 26, in assembled form but without an outer cover structure.

FIG. 28 is a view illustrating an inner frame structure of the water dissipation device of FIG. 26.

FIG. 29 is a top view of the water dissipation device of FIG. 26.

FIGS. 32A-32C illustrate examples of connector ports or couplings for connecting or coupling the water dissipation device of various embodiments of the invention with a breathing circuit.

DETAILED DESCRIPTION

Figure 1:
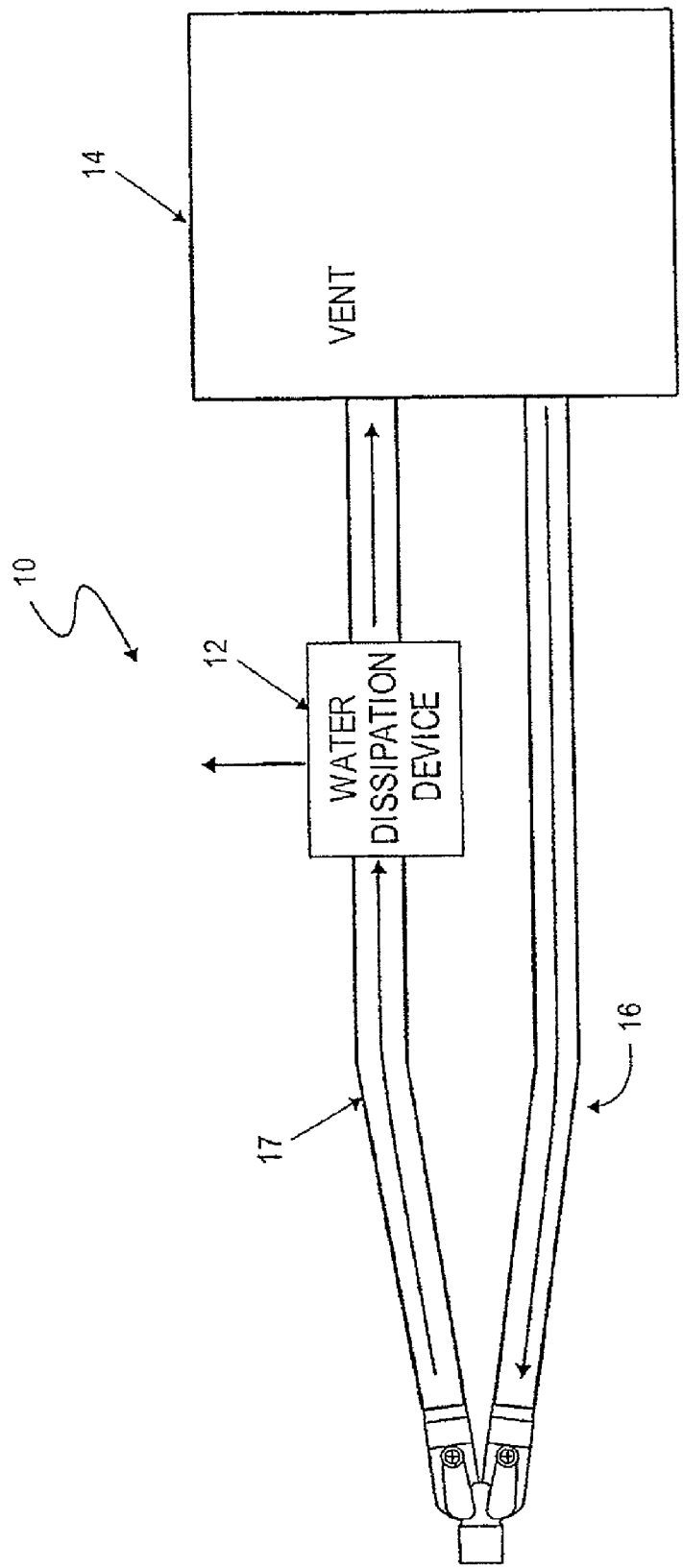
FIG. 1 is a schematic view illustrating a breathing circuit.

The invention will now be described with reference to the drawing figures, in which like parts are referred to with like reference numerals throughout. An embodiment in accordance with the present invention provides a water dissipation device to rapidly remove water vapor or condensate from a humidified medical gas traveling through a breathing circuit between a ventilator and a patient or the patient and the ventilator. The present invention includes a water dissipation device having a housing defining entry and exit ports for coupling to the breathing circuit and a breathable medium permeable to water vapor and impermeable to liquid water, viruses and bacteria enclosed within said housing.

FIG. 1 is a schematic view illustrating a breathing circuit 10 including a water dissipation device 12. The water dissipation device 12 is placed in the breathing circuit 10 between a ventilator 14 and a breathing tube 17 from a patient. The breathing circuit 10 is completed by a second breathing tube 16 extending between the patient and the ventilator. The breathing circuit 10 is a closed system wherein liquid water and/or gases are not able to enter or leave the breathing circuit, except for the release of water vapor. Therefore, the breathing circuit 10 is a closed system except with regard to the passage of water vapor.

Figure 2:
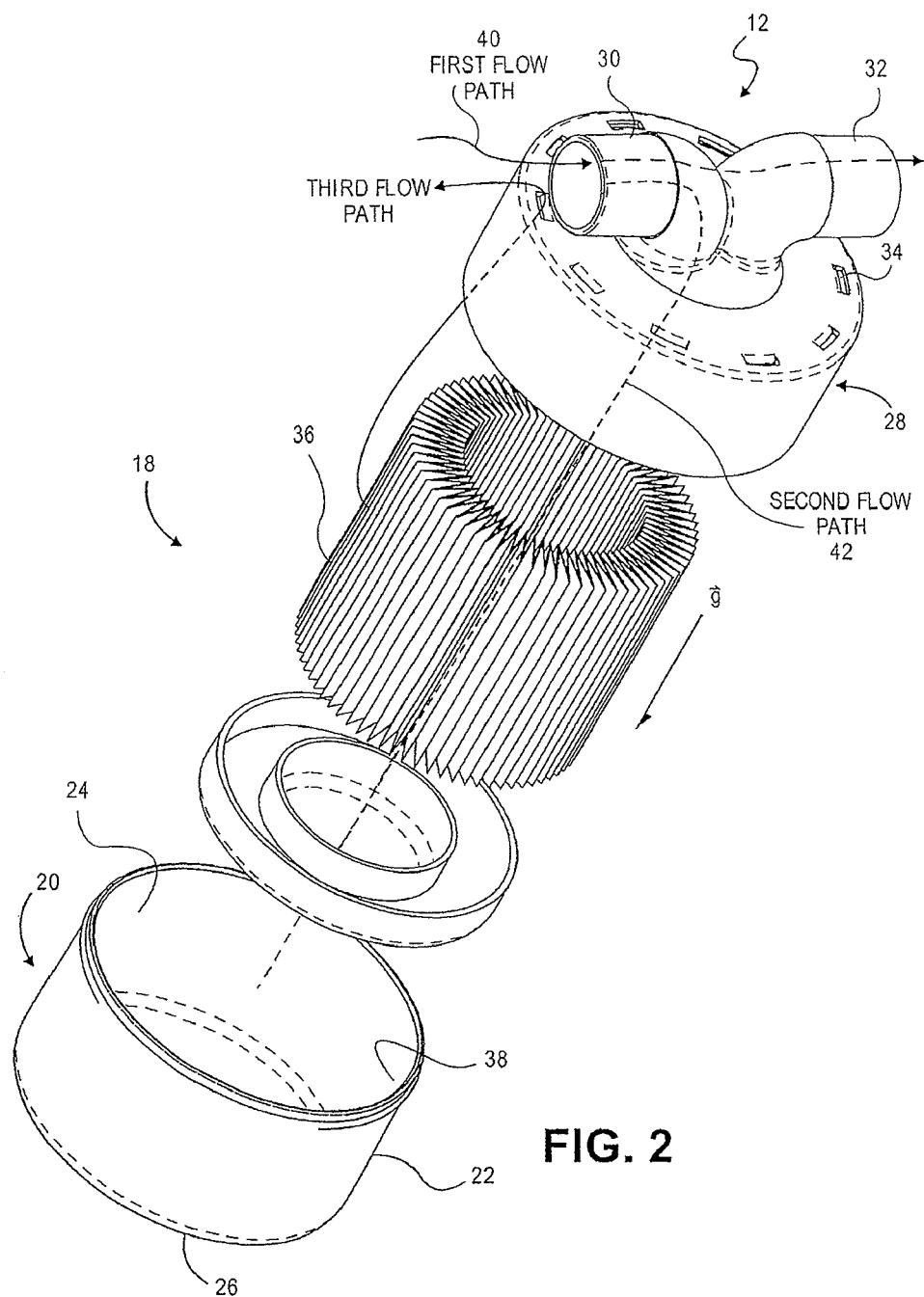
FIG. 2 is an exploded view illustrating a water dissipation device according to an embodiment of the invention.

An embodiment of the present invention is illustrated in FIG. 2. FIG. 2 is an exploded view illustrating the water dissipation device 12 according to a preferred embodiment of the invention. The water dissipation device 12 includes a housing 18 having a cylindrical bottom container 20. The cylindrical bottom container 20 has a side wall 22 that defines a top opening 24 and a bottom surface 26. Also included in the housing 18 is a lid 28 mounted over the top opening 24. The housing 18 defines an entry port 30 and an exit port 32, and more specifically the lid 28 defines the entry port 30 and the exit port 32. The entry port 30 and the exit port 32 allow the water dissipation device 12 to be connected to a breathing circuit, such that the entry port 30 is connected to an expiratory limb of a breathing tube from the patient and the exit port 32 is connected to the rest of the same breathing tube directed toward a ventilator. As shown in FIG. 2, water vapor vents 34 are defined by the housing 18, and more specifically are defined along a periphery of the lid 28. A plurality of the water vapor vents 34 are disposed around an outer edge of a top surface of the lid 28. The lid 28 can also be manufactured from a thermally conductive material to facilitate the cooling of the respiratory gases and increase water condensation.

An annular or tubular breathable medium 36 is enclosed in the housing 18. The tubular breathable medium 36 may be pleated to increase the surface area of the breathable medium within the housing 18. The breathable medium 36 may also line at least a portion of an inside surface 38 of the side wall 22. As used herein, a "breathable medium" is formed of a material that is permeable to water vapor and impermeable to liquid water and gases other than water vapor. The breathable medium 36 allows water vapor to exit the water dissipation device while eliminating the need to open the water dissipation device to empty a reservoir of water and, therefore, allows the system to remain closed.

Figure 3:
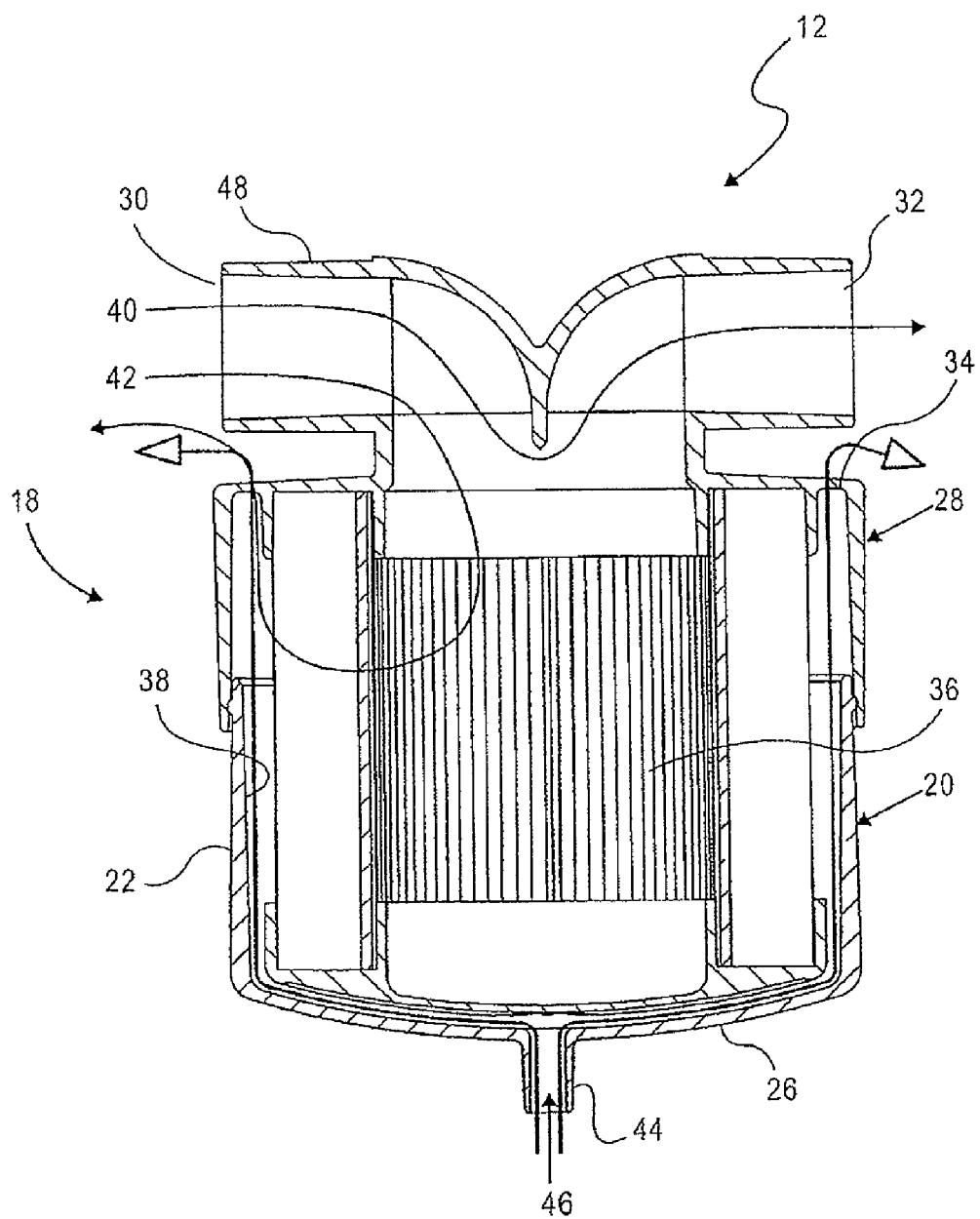
FIG. 3 is a cross sectional view illustrating the embodiment of the water dissipation device illustrated in FIG. 2.

FIG. 3 is a cross sectional view that further illustrates the embodiment of the water dissipation device illustrated in FIG. 2. The housing 18 defines a first flow path 40 of humidified gas between the entry port 30 and the exit port 32. In the first flow path 40, the humidified gas travels into the water dissipation device 12 via the entry port 30, through the housing 18 and exits the water dissipation device 12 via the exit port 32. The first flow path 40 therefore generally corresponds to the main flow path through the water dissipation device along the breathing circuit.

The housing also defines a second flow path 42 for water vapor that extends from the entry port 30 through the tubular breathable medium 36 to at least one opening defined by the housing, other than the exit port 32. In the embodiment shown in FIGS. 2 and 3, this at least one opening includes the water vapor vents 34 defined by the lid of the housing 18. As shown in FIGS. 2 and 3, in the second flow path 42, water vapor in the humidified gas may permeate through breathable medium 36 and exit through the water vapor vents 34. However, liquid water and other gases cannot permeate the breathable medium 36 and exit through the water vapor vents 34.

Additionally, the bottom surface 26 of the outer housing 18 defines an orifice 44 to connect the water dissipation device 12 to an input air source. The housing 18, therefore, defines a third flow path 46 from the orifice 44 through the water dissipation device 12 and out through the water vapor vents 34. The third flow path 46 provides a route for air introduced by the auxiliary compressed dry air input source to blow condensation off of the breathable medium to reduce liquid water collecting in the water dissipation device, and increase the efficiency of the breathable permeable medium. As can be seen in FIG. 2, the annular or tubular breathable medium 36 defines a central channel 37 within which the second flow path 42 may follow.

Figure 4:
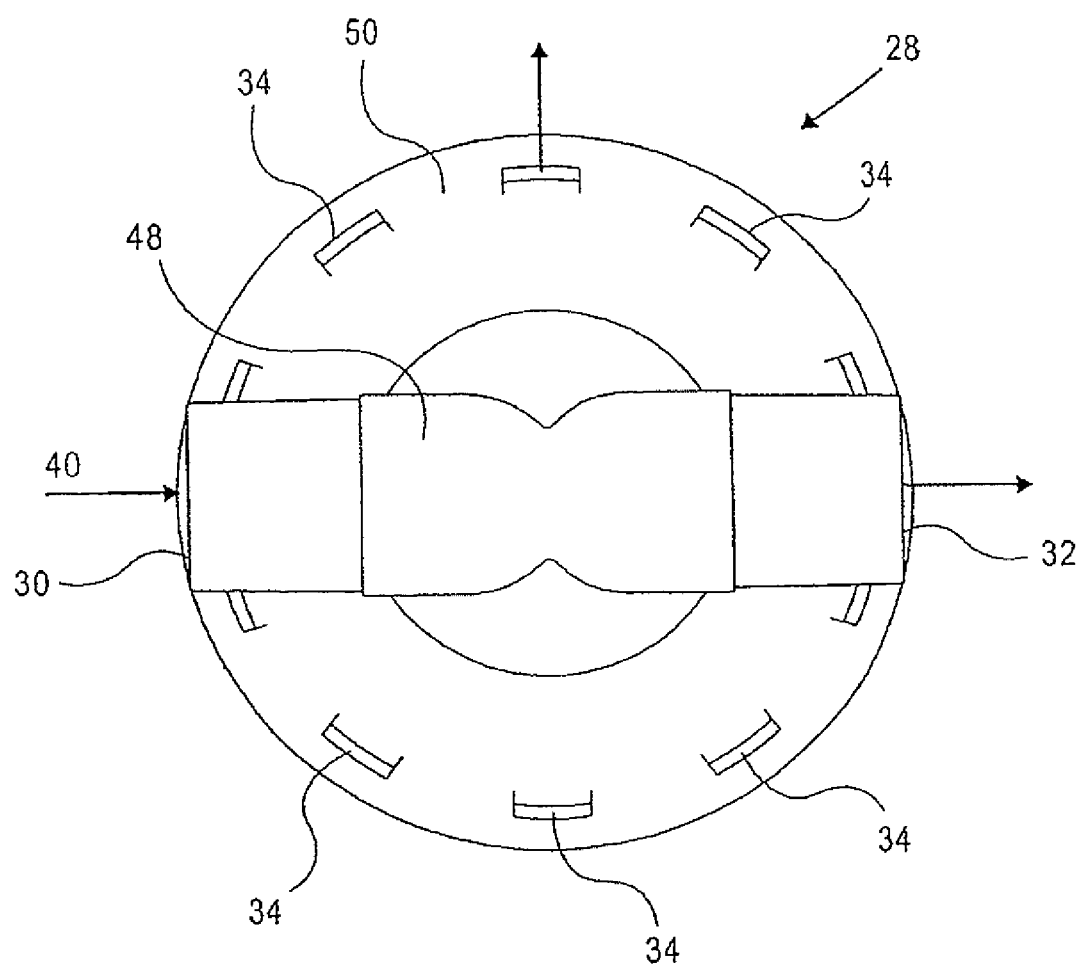
FIG. 4 is a top view of the embodiment of the water dissipation device illustrated in FIGS. 2 and 3.

FIG. 4 is a top view of the lid 28 of the embodiment of the water dissipation device illustrated in FIGS. 2 and 3. FIG. 4 illustrates the entry port 30 and exit port 32 and the water vapor vents 34 in more detail. The entry port 30 and the exit port 32 are disposed on a top surface of the lid 28 and the lid 28 defines a tubular connector portion 48 that couples the water dissipation device 12 to a breathing tube 16. In this embodiment multiple water vapor vents 34 are disposed around the outer edge of the lid 28. However, it is important to note that the number and placement of the water vapor vents 34 are not limited by this embodiment and there may be any number of water vapor vents 34 disposed in any position on the lid 28 or on the remainder of the housing 18.

Figure 5:
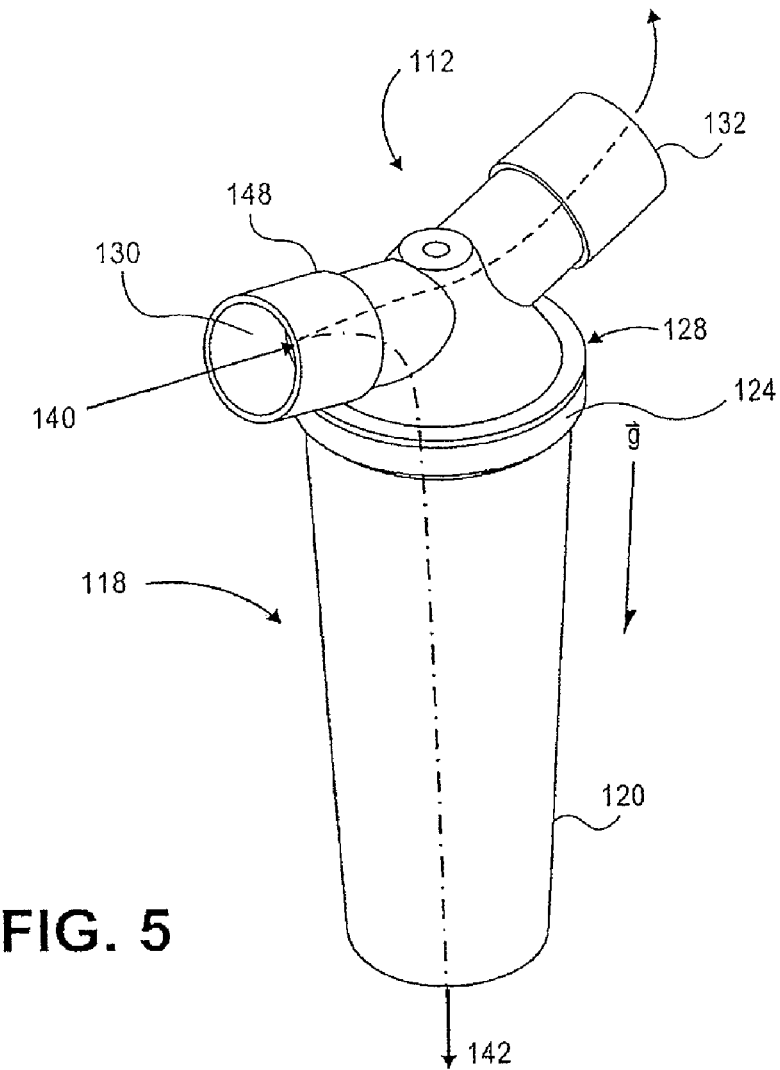
FIG. 5 is a three-quarter view illustrating the water dissipation device according to another embodiment of the present invention.

Another embodiment of the present invention is illustrated in FIG. 5. FIG. 5 is a three-quarter view illustrating a water dissipation device 112 according to another embodiment of the present invention. In this embodiment, the housing 118 includes a cylindrical bottom container 120 that has side wall 122 defining a top opening 124. The housing also includes a lid 128 that is mounted on the top opening 124. Additionally, the housing 118 defines an entry port 130 and an exit port 132.

Figure 6:
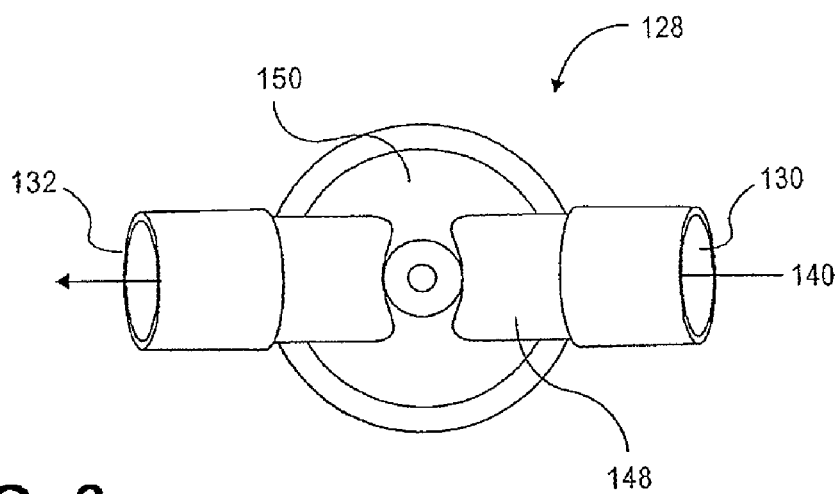
FIG. 6 is a top view of the embodiment illustrated in FIG. 5.

FIG. 6 is a top view of the embodiment illustrated in FIG. 5. FIG. 6 illustrates in more detail the lid 128 and the entry port 130 and the exit port 132. Preferably, the lid 128 is the portion of the housing that defines the entry port 30 and the exit port 132. The entry port 130 and the exit port 132 are disposed on the top surface 150 of the lid 128 and include a tubular connector portion 148 that couples the water dissipation device 112 to a breathing tube.

Figure 7:
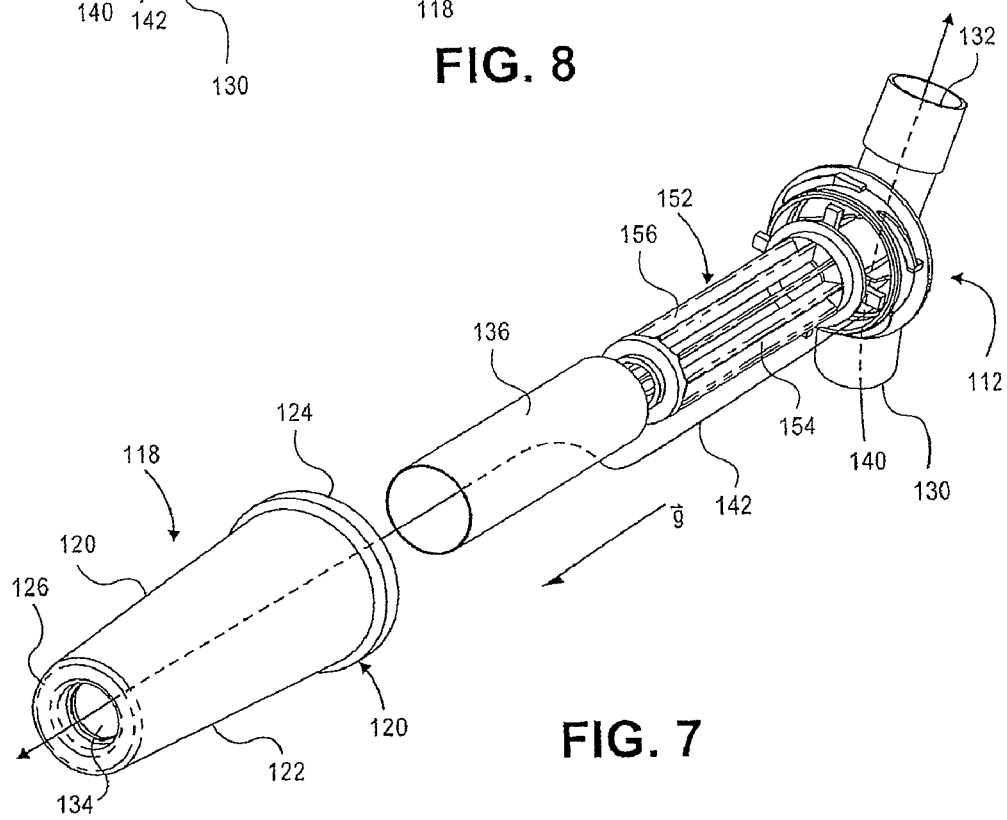
FIG. 7 is an exploded view of the embodiment illustrated in FIGS. 5 and 6.

FIG. 7 is an exploded view of the embodiment illustrated in FIGS. 5 and 6. FIG. 7 illustrates in more detail the structure of the housing 118 and the tubular breathable medium 136. Threads on the lid 128 as well as corresponding threads on the cylindrical bottom container 120 couple the lid 128 to the cylindrical bottom container 120, such that there is an air tight seal between them.

Additionally, the lid 128 has a tubular cage 152 that extends into the cylindrical bottom container 20 of the housing 18. The tubular cage 152 has fins 154 that extend along the span of the housing 118. The fins 154 are separated by longitudinal openings or spaces that define water vapor vents 156 between the fins 154. An annular or tubular breathable medium 136 is also disposed within the cylindrical bottom container 120, and it is positioned between the tubular cage 152 and the sidewalls 122 of the cylindrical bottom container 120 of the outer housing 118.

Figure 8:
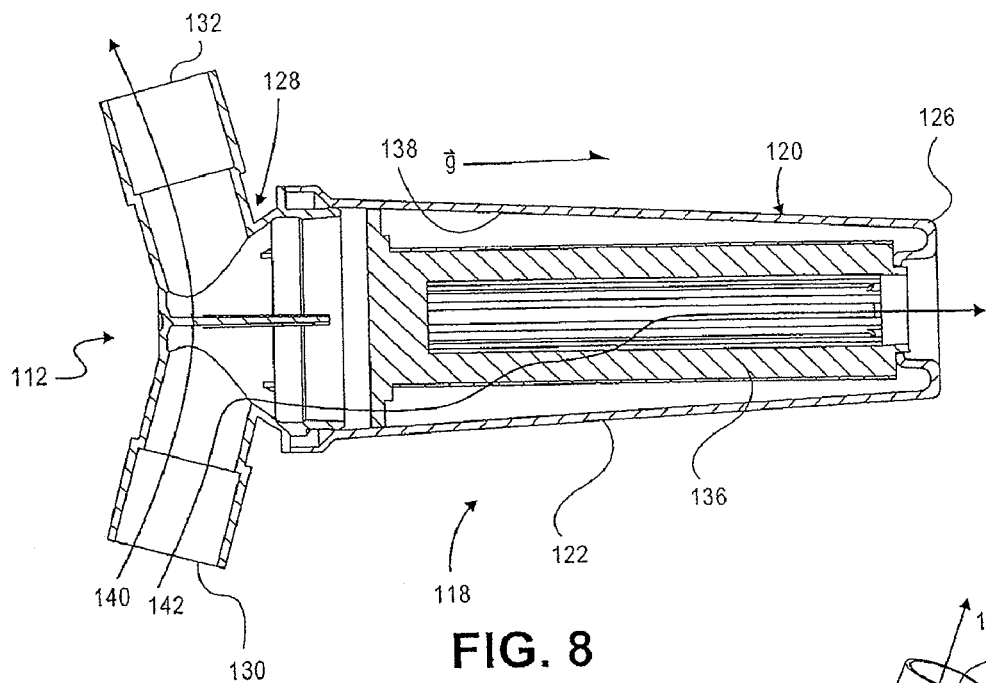
FIG. 8 is a cross sectional view of the embodiment illustrated in FIGS. 5-7.

FIG. 8 is a cross sectional view of the embodiment illustrated in FIGS. 5 through 7. FIG. 8 illustrates the housing 118 and the breathable medium 136 in a fully assembled condition. The lid 128 and the cylindrical bottom container 120 couple together to form an air tight seal. With reference to the gravity vector g shown in FIGS. 7 and 8 for the preferred orientation of the device 112 when inserted into a breathing circuit, the tubular cage 152 extends from a bottom surface of the lid 128 to the bottom surface 126 of the cylindrical bottom container 120. The tubular breathable medium 136 is disposed around and supported by the tubular cage 152.

A first flow path 140 is defined by the housing 118 and extends through the water dissipation device 112 directly from the entry port 130 and through to the exit port 132 as shown in FIGS. 7 and 8. The humidified gas generally flowing through the breathing circuit to which the device of the present invention is attached can therefore travel through the water dissipation device 112 via the first flow path 140. A second flow path 142 is also defined by the housing 118 and extends from the entry port 130 through the tubular breathable medium 136 and out of the water dissipation device 112 via the water vapor vents 156 defined by the fins 154 of the tubular cage 152. Water vapor in the humidified gas may permeate the breathable medium 136 to exit through the water vapor vents 156, but liquid water, bacteria, viruses and other gases cannot permeate the breathable medium 136. It will be noted in FIGS. 7-8 that the second flow path provides for water vapor permeation from the outer surface to the inner surface of the tubular breathable medium 136. Breathable medium 136 defines a central channel 137 through which the final portion of the second flow patent 142 flows.

FIGS. 9, 10 and 11 illustrate another embodiment of the water dissipation device of the present invention. In this embodiment, the housing 218 defines the entry port 130 and exit port 132 for coupling a water dissipation device 212 to a breathing circuit. Preferably, in this embodiment, the housing 218 has a cylindrical bottom container 120 having a side wall 122 that defines a top opening 124. The lid 128 is mounted on the top opening 124 and preferably defines the entry port 130 and the exit port 132. The housing 218 also defines an opening 160 in a bottom surface 161 of the housing 218. A flat disk breathable medium 262 is disposed in said housing 218 and covers the opening 160 in the bottom surface of the housing 218.

A first flow path 140 between the entry port 130 and the exit port 132 is defined by the housing 218. The housing 218 also defines a second flow path 242 from the entry port 130 through the housing 218 and out through the opening 160 and flat disk breathable medium 262 on the bottom surface 161 of the cylindrical bottom container 120. Only water vapor passes through the flat disk breathable medium 262 because it is permeable to water vapor but impermeable to liquid water, bacteria, viruses and other gases.

Figure 12:
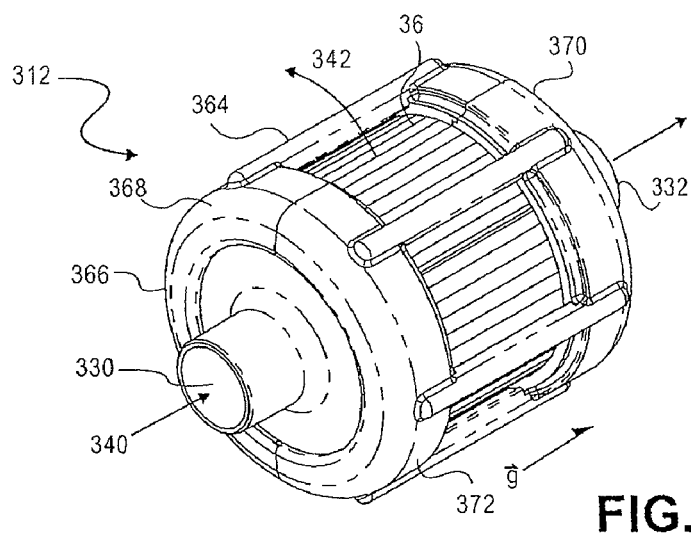
FIG. 12 is a side view illustrating another embodiment of the present invention.
Figure 13:
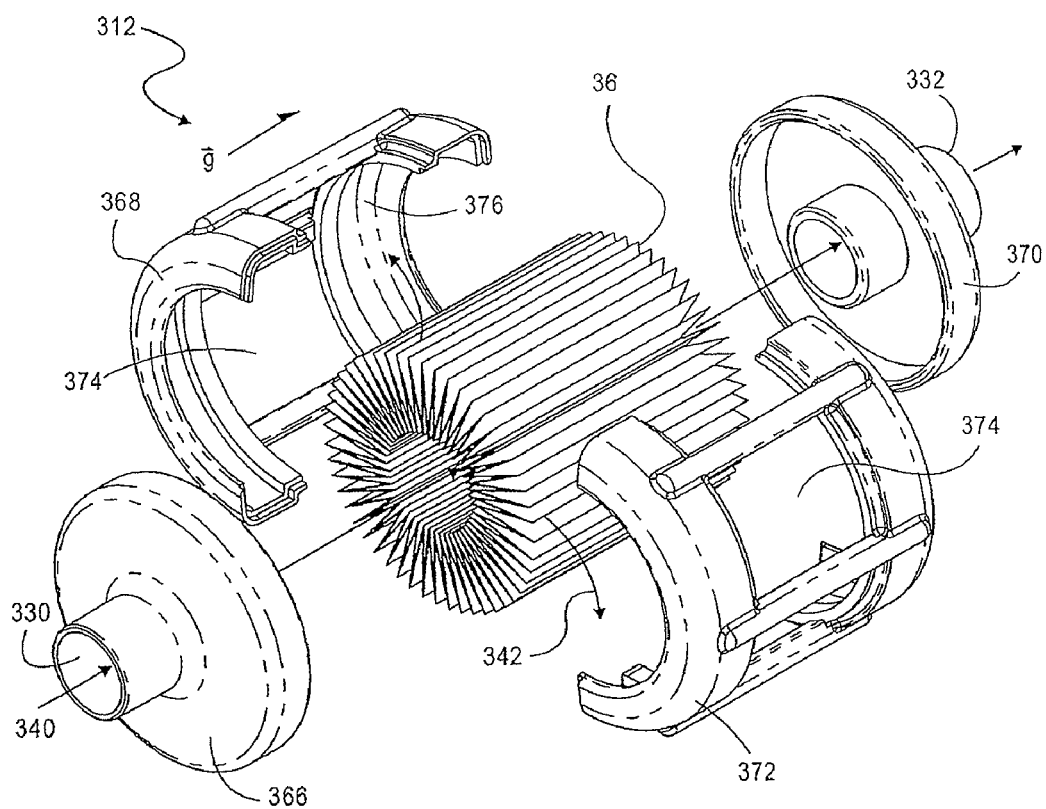
FIG. 13 is an exploded view of the embodiment illustrated in FIG. 12.

FIG. 12 illustrates a side view of another embodiment of the water dissipation device of the present invention. FIG. 13 illustrates an exploded view of the embodiment illustrated in FIG. 12. In this embodiment, a water dissipation device 312 has a cylindrical caged body 364 that encloses an annular or tubular breathable medium 336. The cylindrical caged body 364 is formed of two halves 368 and 372, which can be separable. The water dissipation device 312 has a first end cap 366 defining the entry port 330. A second end portion 370 defines the exit port 332. The circular end caps 366 and 370 are held in place inside complementary grooves on the inside of portions of the caged body halves 368 and 372. A plurality of windows 374 are defined by the cylindrical caged body 364 to allow for egress of water vapor from the water dissipation device 312.

The cylindrical caged body 364 encloses a tubular breathable medium 336 which lines at least a portion of an inside surface 376 of the cylindrical caged body 364. Preferably, the tubular breathable medium 336 is pleated and permeable to water vapor but impermeable to liquid water, bacteria, viruses and other gases. However, the breathable medium 36 should not be limited by this description and may take various forms or positions within the cylindrical caged body 364.

The cylindrical caged body 364 defines a first flow path 340 between the entry port 330 and the exit port 332. Additionally, the cylindrical caged body 364 defines a second flow path 342 from the entry port 330, through the breathable medium 336 and out of the water dissipation device 312 via the windows 374 in the cylindrical caged body 364. Only water vapor passes through the tubular breathable medium 36 in the second flow path 342.

Figure 14:
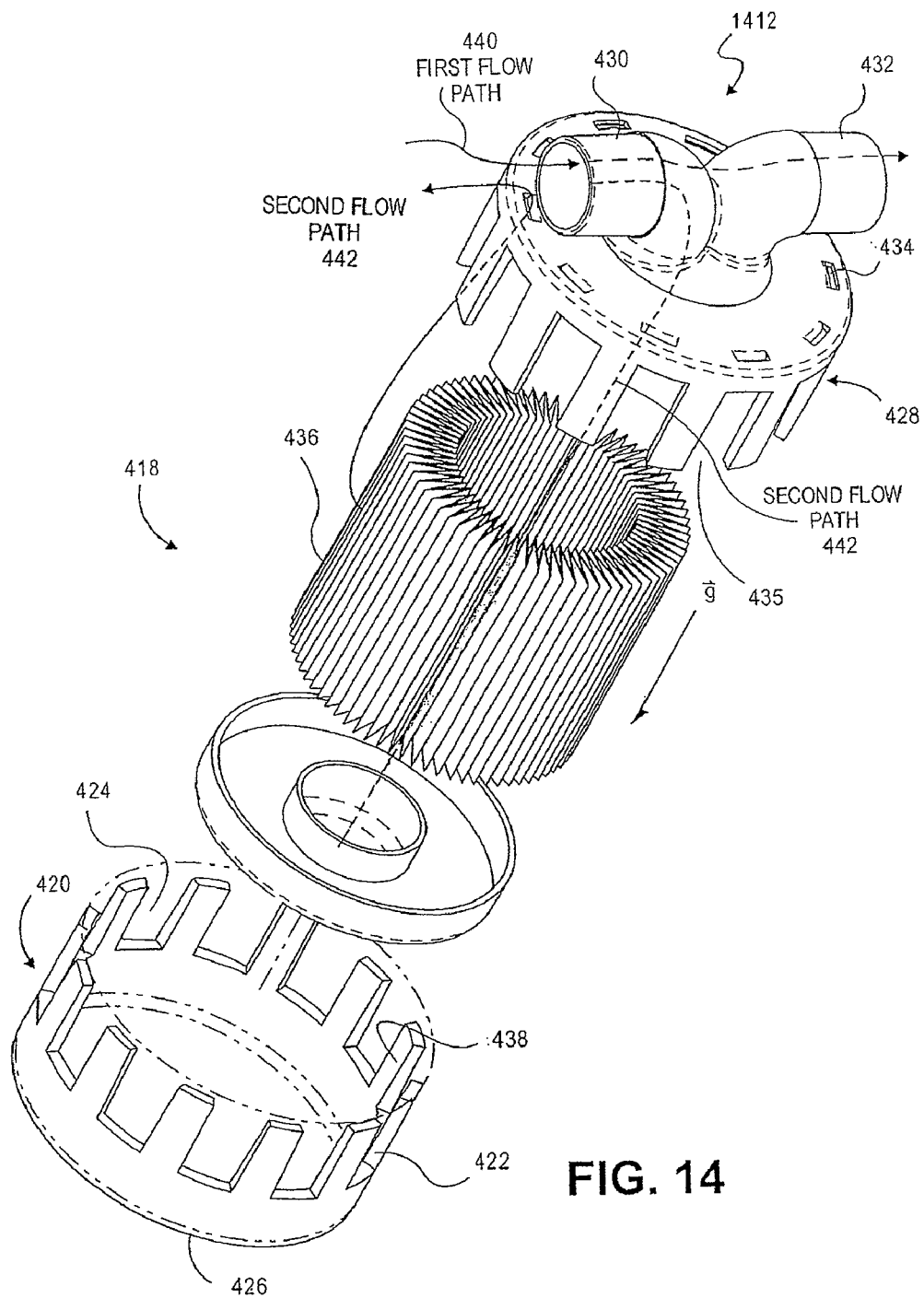
FIG. 14 is an exploded view illustrating another embodiment of the present invention.

An embodiment of the present invention is illustrated in FIG. 14. FIG. 14 is an exploded view illustrating the water dissipation device 412 according to a preferred embodiment of the invention. The water dissipation device 412 includes a housing 418 having a caged cylindrical bottom container 420. The caged cylindrical bottom container 420 has a side wall 422 that defines a top opening 424 and a bottom surface 426. Also included in the housing 418 is a lid 428 mounted over the top opening 424. The housing 418 defines an entry port 430 and an exit port 432, and more specifically the lid 428 defines the entry port 430 and the exit port 432. The entry port 430 and the exit port 432 allow the water dissipation device 412 to be connected to a breathing circuit, such that the entry port 430 is connected to an expiratory limb of a breathing tube from the patient and the exit port 432 is connected to another tube directed toward a ventilator. As shown in FIG. 14, water vapor vents 434 are defined by the housing 418, and more specifically are defined along a periphery of the lid 428. The cylindrical bottom container 420 and the lid 428 also define windows 435 which allow for egress of water vapor from the water dissipation device 412. The lid 428 can also be manufactured from a thermally conductive material to facilitate the cooling of the respiratory gases and increase water condensation.

A tubular breathable medium 436 is enclosed in the caged housing 418. The tubular breathable medium 436 may be pleated to increase the surface area of the breathable medium within the housing 418 and may also be perforated. The breathable medium 436 may also line at least a portion of an inside surface 438 of the side wall 422. The breathable medium 436 is formed of a material that is permeable to water vapor and impermeable to liquid water and other gases. The breathable medium 436 allows water vapor to exit the water dissipation device while eliminating the need to open the water dissipation device to empty a reservoir of water and, therefore, allows the system to remain closed.

Figure 15:
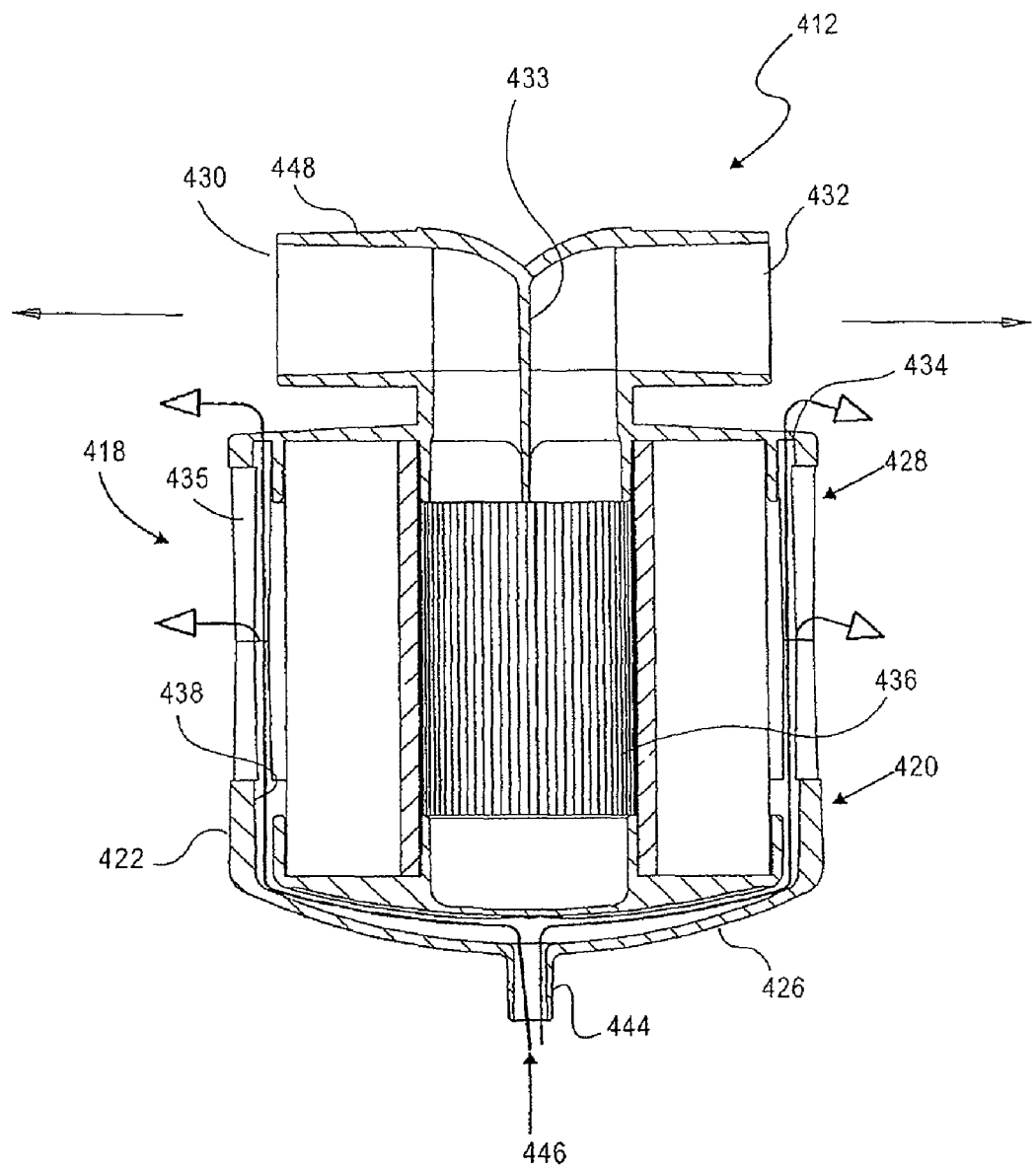
FIG. 15 is a cross-sectional view of the embodiment illustrated in FIG. 14.

FIG. 15 is a cross sectional view that further illustrates the embodiment of the water dissipation device illustrated in FIG. 14. The caged housing 418 defines a first flow path 440 of humidified gas between the entry port 430 and the exit port 432. In the first flow path 440, the humidified gas travels into the water dissipation device 412 via the entry port 430, through the housing 418 and exits the water dissipation device 412 via the exit port 432. The first flow path 440 therefore generally corresponds to the main flow path through the water dissipation device along the breathing circuit, except that in this embodiment, a partition or baffle element 433 extends in the housing 418 perpendicular to the axis through the entry and exit ports 430 and 432, which causes to further define the first flow path 440 to extend farther into the housing 418 and nearer to the channel 437 formed inside the annular breathable medium 436.

The housing also defines a second vapor or flow path 442 that extends from the entry port 430 through the tubular breathable medium 436, and then out to either the water vapor vents 434 defined by the housing 418, or out of the housing 418 through the windows 435. However, liquid water and other gases cannot permeate the breathable medium 436 and exit through the windows 435.

Additionally, the bottom surface 426 of the outer housing 418 defines an orifice 444 to connect the water dissipation device 412 to an input air source. The housing 418, therefore, defines a third flow path 446 from the orifice 444 through the water dissipation device 412 and out through the water vapor vents 434, or out through the windows 435. The third flow path 446 provides a route for air introduced by the auxiliary compressed dry air input source to blow condensation off of the breathable medium to reduce liquid water collecting in the water dissipation device, and increase the efficiency of the breathable permeable medium.

Figure 16:
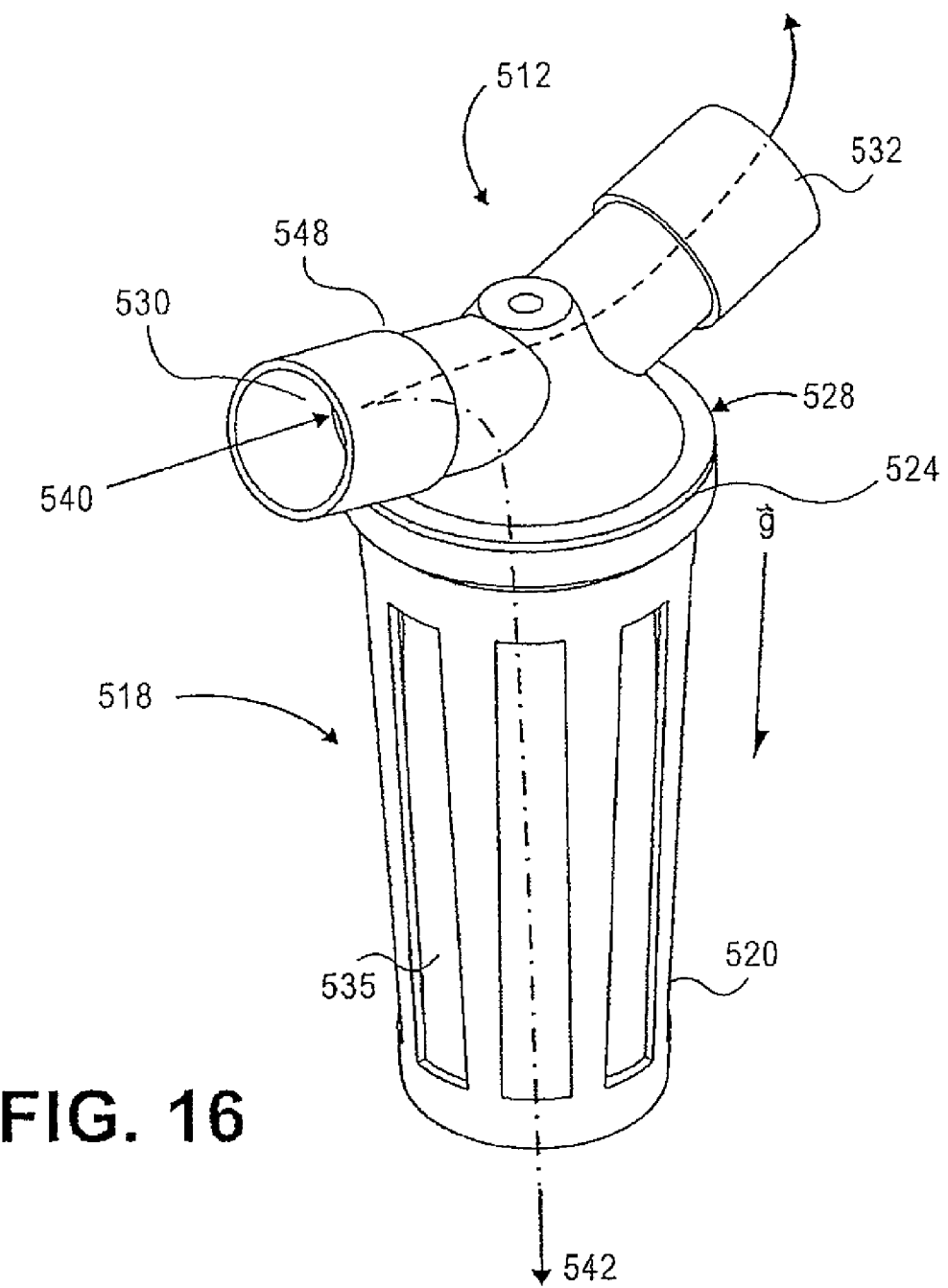
FIG. 16 is a three-quarter view illustrating another embodiment of the present invention.

Another embodiment of the present invention is illustrated in FIG. 16. FIG. 16 is a three-quarter view illustrating a water dissipation device 512 according to another embodiment of the present invention. In this embodiment, the housing 518 includes a caged cylindrical bottom container 520 that has side wall 522 defining a top opening 524. The housing also includes the lid 528 that is mounted on the top opening 524. Additionally, the housing 518 defines an entry port 130 and an exit port 532. As shown in the embodiment in FIG. 16, the side wall 522 of the caged cylindrical bottom container 520 defines a plurality of windows 535. An annular or tubular breathable medium is encased inside the cage structure of the housing 518 against the sidewalls 522. A first flow path 540 flows from the entry port 540 through to the exit port 532, while a second water vapor flow path 542 flows from the entry port 540 down into the housing 518 though a central channel defined by the annular breathable medium 536, and then out through the breathable medium 536 and the windows 535.

Figure 17:
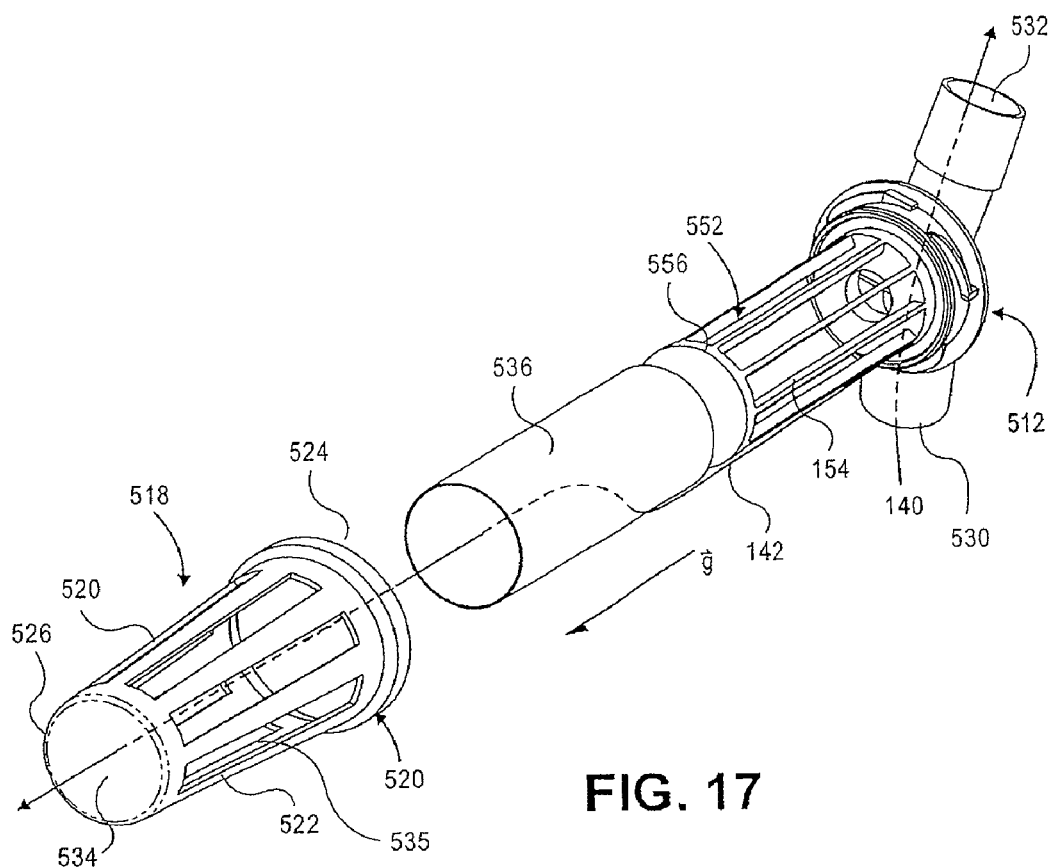
FIG. 17 is an exploded view of the embodiment illustrated in FIG. 16.

FIG. 17 is an exploded view of the embodiment illustrated in FIG. 16. FIG. 17 illustrates in more detail the structure of the housing 518 and the tubular breathable medium 536. Threads on the lid 528 as well as corresponding threads on the cylindrical bottom container 520 couple the lid 528 to the cylindrical bottom container 520.

Additionally, the lid 528 has a tubular cage 552 that extends into the cylindrical bottom container 520 of housing 518. The tubular cage 552 has fins 554 that extend along the span of the housing 518. The fins 554 are separated by longitudinal openings or spaces that define water vapor vents 556 between the fins 554. The tubular cage 552 has a flat disk 553 to form a bottom for the tubular cage 552. A tubular breathable medium 536 is also disposed within the cylindrical bottom container 520, and it is positioned between the tubular cage 552 and the cylindrical bottom container 520 of the outer housing 518.

Figure 18:
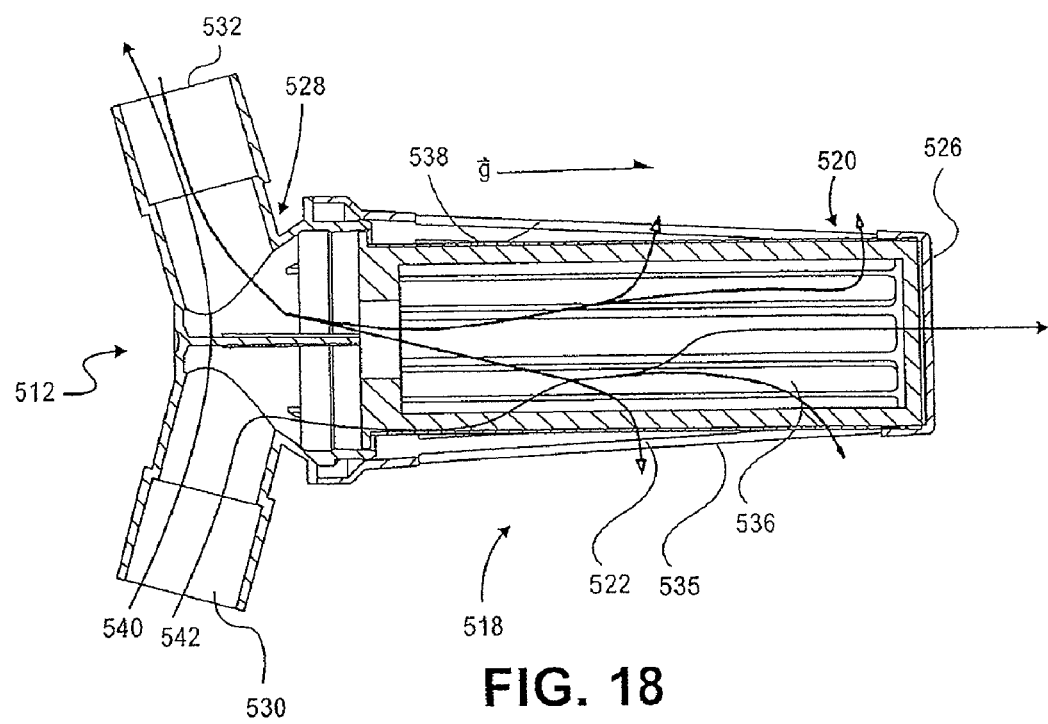
FIG. 18 is a cross-sectional view of the embodiment illustrated in FIGS. 16 and 17.

FIG. 18 is a cross sectional view of the embodiment illustrated in FIGS. 16 and 17. FIG. 18 illustrates the housing 518 and the breathable medium 536 in a fully assembled condition. The lid 528 and the cylindrical bottom container 520 couple together. The tubular cage 552 extends from a bottom surface of the lid 528 to the bottom surface 526 of the cylindrical bottom container 520. The tubular breathable medium 536 is disposed around and supported by the tubular cage 552.

A first flow path 540 is defined by the housing 518 and extends through the entry port 530, through the water dissipation device and through the exit port 532. The humidified gas generally flowing through the breathing circuit to which the device of the present invention is attached can therefore travel through the water dissipation device 512 via the first flow path 540. A second water vapor flow path 542 is also defined by housing 518 and extends from entry port 530 through tubular breathable medium 536 and out of the water dissipation device 512 via the water vapor vents 556 defined by the fins 554 of the tubular cage 552 and out through the windows 535 defined by the caged cylindrical bottom container 520. Water vapor in the humidified gas may permeate the breathable medium 536 to exit through the water vapor vents 556, but liquid water, bacteria, viruses and other gases cannot permeate the breathable medium 536. An alternative embodiment of the device shown in FIGS. 17 and 18 could also omit the bottom caged cylindrical housing body 520 such that the second flow path 542 flowed directly through breathable medium 536 out to the surroundings.

Figure 19:
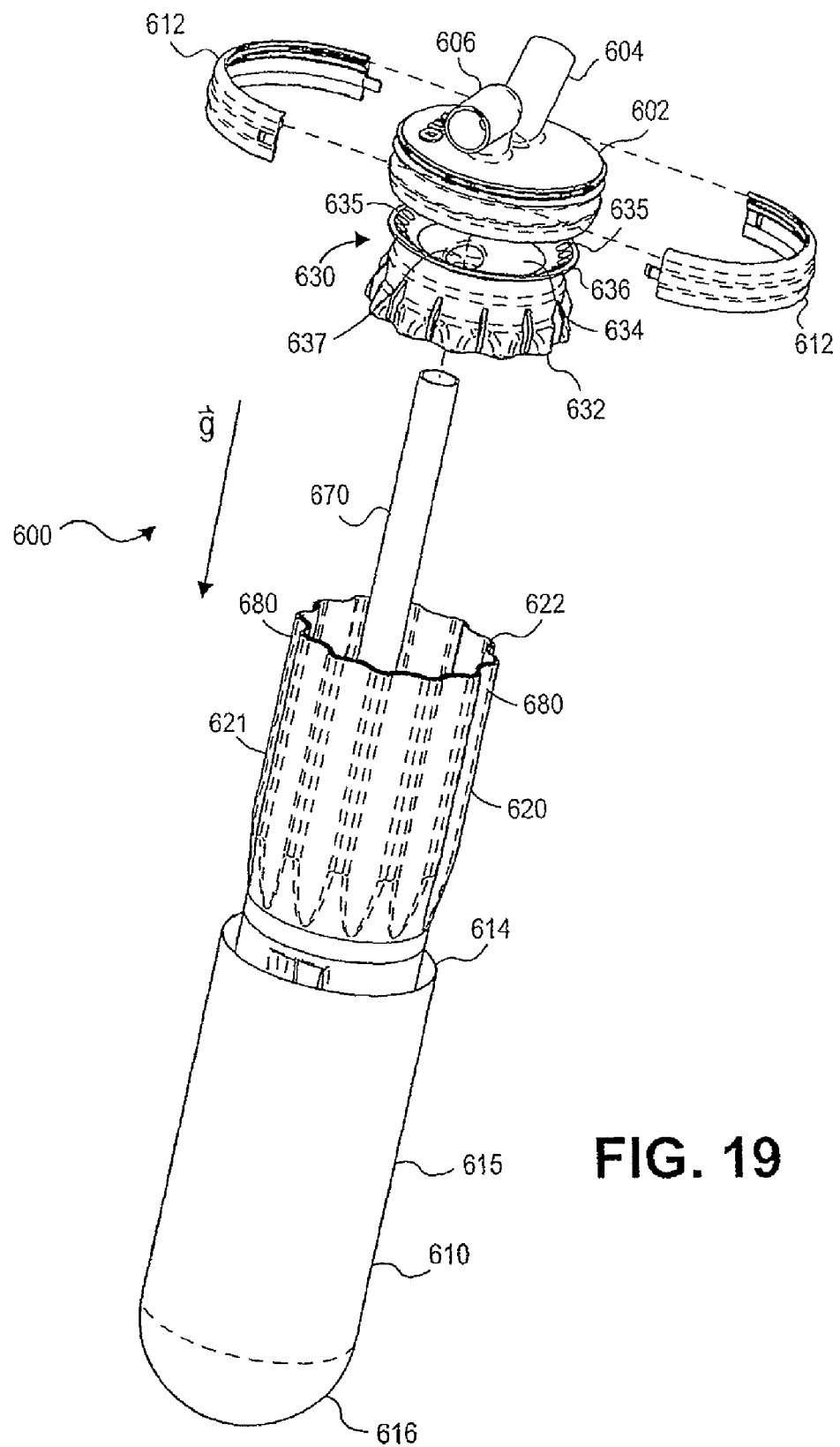
FIG. 19 is an exploded view of a water dissipation device in accordance with another embodiment of the invention.

FIG. 19 is an exploded view of a water dissipation device in accordance with another embodiment of the invention. The inventive device is shown relative to a gravity vector "g" as shown, such that "upper" and "lower" portions of the device are construed relative to said vector, "upper" being in the opposite direction from vector g, and "lower" being in the direction of vector g. The invention includes a water dissipation device 600 having an upper lid structure 602 defining an entry port 604 and an exit port 606 for coupling the device to a breathing circuit. The water dissipation device 600 is preferably placed at the end of the expiratory limb of a breathing circuit before the ventilator, although the positioning can be anywhere along a breathing circuit.

A cover or cover structure 610 is attached or coupled to the upper lid 602 via any means, but can include, in the embodiment shown in FIG. 19, a pair of semi-circular securing ring clamps or arc structures 612 which matingly fit around the perimeter of upper lid 602. The cover structure 610 is a cover element which can be described as a hollow, bag-shaped or bucket-shaped element defining a top opening 614 and closed bottom 616. The walls of cover structure 610 can have any width or thickness, but are relatively thin and can be flexible, such as a membrane. Alternatively, the cover structure 610 can be rigid and relatively inflexible. The material of cover structure 610 has a first inner layer made of water or moisture wicking material, and a second outer layer surrounding the first inner layer, the second outer layer made of a water vapor breathable medium. The cover structure 610 is therefore a moisture accumulation and water vapor transfer means, providing a pathway for water vapor to exit a breathing circuit via flow into the water dissipation device 600 and through the cover structure 610.

The structural arrangement of the parts of the water dissipation device 610 are such that the device defines an inner flow space or series of flow spaces fluidly coupled to the entry port 604 and exit port 606. Furthermore, because of the water vapor breathable medium in the cover element 610, water vapor can also flow from inside of the device out to the environment surrounding the device, providing a flow path for water vapor to exit a breathing circuit to which the water dissipation device 610 is coupled. This provides a way to reduce the water vapor and moisture content which can build up in a breathing circuit when it is connected to a patient.

Figure 20:
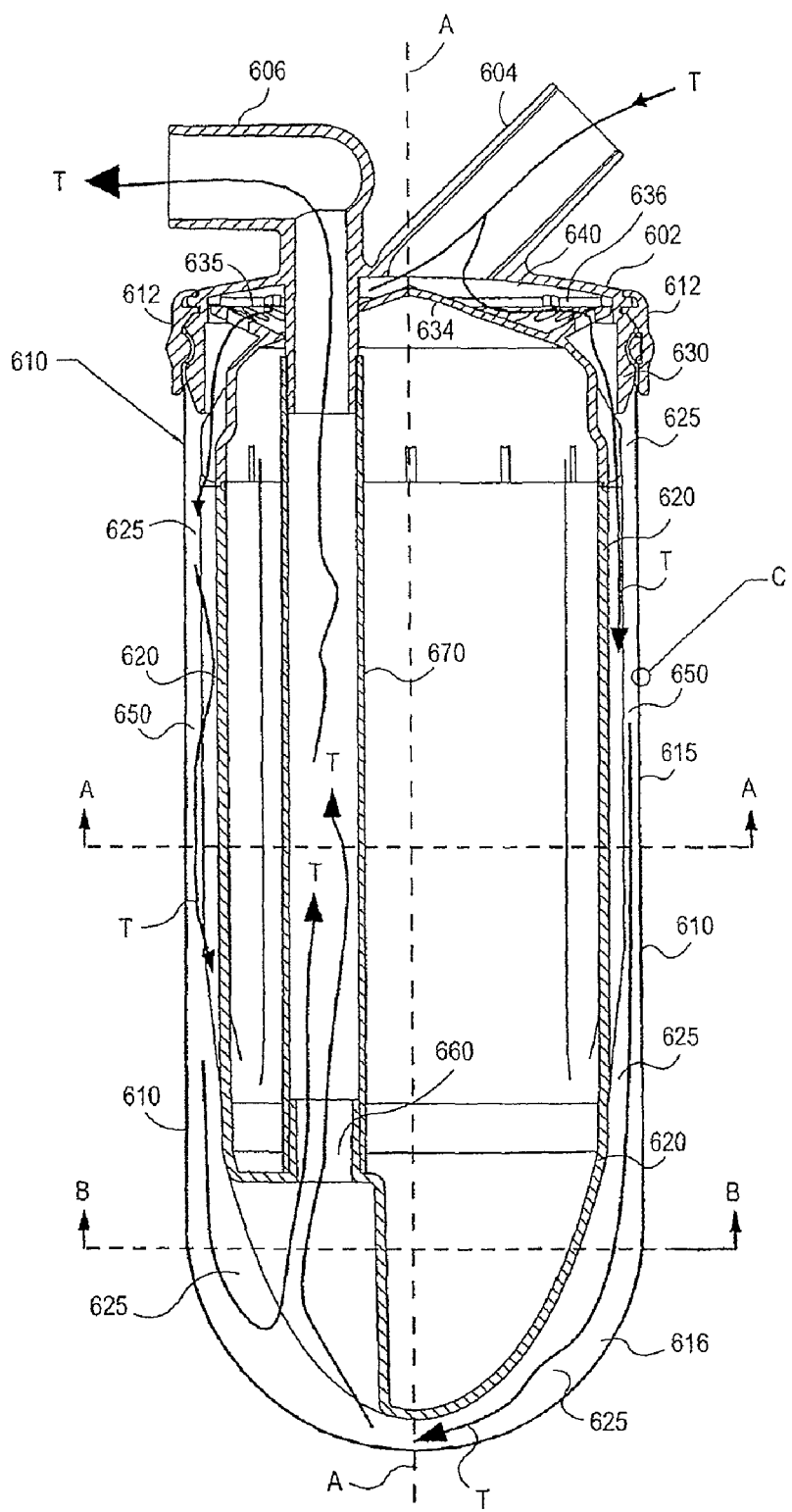
FIG. 20 is a cross-sectional view of the assembled water dissipation device shown in FIG. 19, showing some of the flow paths for fluid flowing through the device.

FIG. 20 is a cross-sectional view of the assembled water dissipation device 600, showing some of the flow paths for fluid flowing through the device. As also shown in FIG. 19, an inner frame element 620 is enclosed by the cover structure 610. The shape of the cover structure 610 is such that it narrowly surrounds the inner frame 620 to define an inner flow space 625 which is at least partially disposed between the inner frame and cover structure. The inner frame 620 is large enough relative to the cover structure 610 that it encloses a majority of a volume enclosed by the cover structure. This provides a set of narrow and annular flow spaces in the inner flow space 625 between the walls of the inner frame 620 and cover structure 610. The arrangement of the inner frame 620 inside of the cover structure 610 also reduces the overall volume or the inner flow space 625 and consequently the compliance of the device 600 when connected to a breathing circuit.

The flow paths provided by the inner flow space 625 are at least partially bounded by the inner layer of water or moisture wicking material in the cover element 610. When the device 600 is coupled to a breathing circuit (not shown) via entry port 604, humidified gases flow through the inner flow space 625 along arrows T as shown in FIG. 20. The inner flow space 625 is tortuous and includes a number of different spaces and volumes all fluidly coupled together which wind around the inner frame 620. An upper cap 630 is also included which is positioned within the volume created when the upper lid 602 and cover element 610 are attached together. The upper cap 630 is shaped to have a lower end with a perimeter 632 which mates to the upper opening or perimeter 622 of the inner frame 620. The upper cap 630 is covered over its upper surface 634 by the upper lid 602 defining a volume or space 640 therebetween. Flow T from a breathing circuit coupled to the entry port 604 thereby flows through to the space 640 between the upper lid 602 and upper cap 630 and then impinges against upper surface 634 of the upper cap 630 and is radially distributed out from the central axis A to a plurality of holes 635 defined by a rim 636 on the perimeter of the upper cap 630. This distributes the flow T from the entry port 604 into a generally annular volume portion 650 of the inner flow space 625 defined between the inner frame 620 and cover 610. The upper cap 630 can therefore be characterized as an inner flow dispersal lid element disposed between the inner frame 620 and upper lid 602 and adjacent an upper end of the annular volume 650, the inner flow dispersal lid element 630 defining the plurality of openings 635 for dispersing flow received through the entry port 604 into the annular volume 650 of the inner flow space 625 of the device 600.

Figure 21:
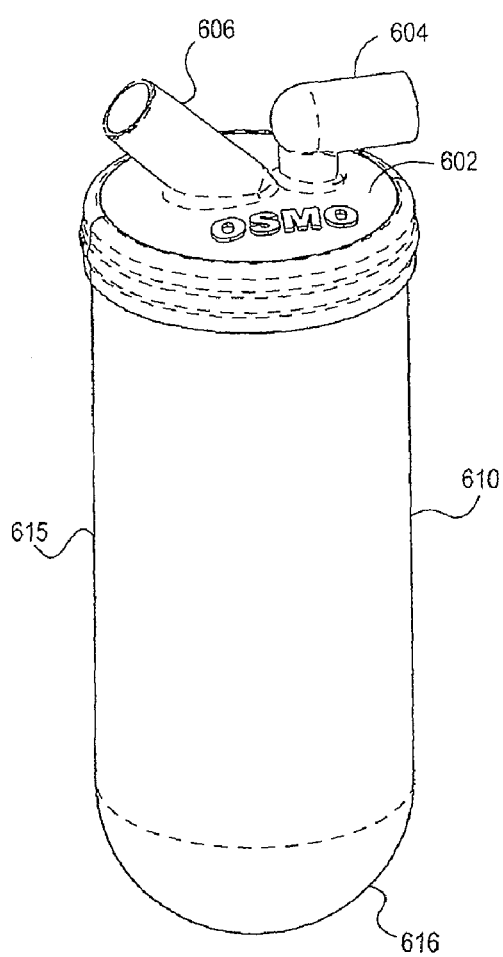
FIG. 21 is an exterior view of the assembled water dissipation device in FIG. 19.

As shown in FIG. 19, the cover structure 610 can have a substantially cylindrical portion 615 between its open top end 614 and closed bottom end 616 and the inner frame 620 can have a substantially cylindrical portion 621 enclosed by the substantially cylindrical portion 615 of the cover structure. By "substantially cylindrical" it is understood that deviations from a cylindrical shape are possible, such that elliptical, oval, rectangular, square, or other cross-sectional shapes are possible for the cover structure 610 and inner frame 620. In the preferred embodiment shown in FIGS. 19 and 20, the cover structure 610 and inner frame 620 are substantially cylindrical such that each element encloses a relatively large volume in relation to its outer surface area, in accordance with the geometric properties of a cylinder. FIG. 21 is an exterior view of the assembled water dissipation device 600 in FIG. 19.

Between the two substantially cylindrical elements 610 and 620 a substantial portion of the inner flow space 625 is disposed, including a plurality of long narrow flow spaces in an annular arrangement around central axis A of the device 600 shown in FIG. 20. The inner frame 620 also defines a lower opening 660 proximate the lower end 616 of the cover 610. As best shown in FIG. 20, the lower opening 660 is in fluid communication with the annular volume 650 and the exit port 606 defined by the upper lid 602 via a tube 670 which is surrounded by the inner frame 620. The inner frame 620 can further include a plurality of longitudinal ribs 680 along an outside surface of its cylindrical portion 621 which can, in one embodiment, support the cover element 610. The annular volume 650 can be separated into one or more longitudinal channels 685 defined between the inner frame 620 and cover element 610, each channel being longitudinally bounded by two longitudinal ribs 680. This is best shown in FIGS. 20A and 20B, which are transverse sectional views of the assembled water dissipation device shown in FIG. 19, taken along sections A-A and B-B, respectively, in FIG. 20.

Figure 20C:
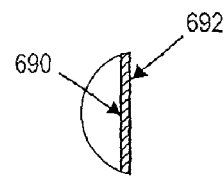
FIG. 20C is a schematic magnified view of a portion the assembled water dissipation device shown in FIG. 19, taken from area C in FIG. 20.
Figure 20A:
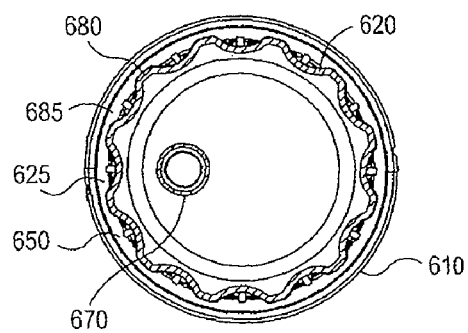
FIG. 20A is a transverse sectional view of the assembled water dissipation device shown in FIG. 19, taken along section A-A in FIG. 20.
Figure 20B:
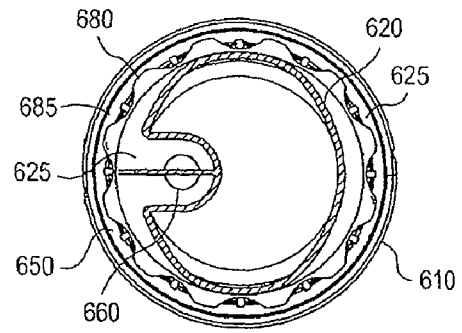
FIG. 20B is a transverse sectional view of the assembled water dissipation device shown in FIG. 19, taken along section B-B in FIG. 20.

FIG. 20C is a schematic magnified view of a portion of the walls of cover structure 610, taken from area C indicated in FIG. 20, which shows inner layer 690 of water or moisture wicking material and outer layer 692 of water vapor breathable medium which make up cover structure 610. Both inner layer 690 and outer layer 692 are water vapor breathable in that both allow passage of water vapor. However inner layer 690 is made of wicking material which allows for adsorption and/or absorption of both moisture and water in any phase, gas or liquid, using a capillary action, while the water vapor breathable medium of outer layer 692 permits the passage of water vapor only and not liquid water. Examples of wicking material in inner layer 690 are a knit or non-woven cloth or fabric, made of polyester, polyester and polypropylene blends, nylon, polyethylene or paper, and can be microfilaments or microfiber material such as Evolon® brand fabric material made by Freudenberg & Co. KG. A particular example of wicking material would be a non-woven material of 70% polypropylene and 30% polyester. Examples of outer layer 692 of water vapor breathable medium are Sympatex®M brand water vapor permeable membranes made of polymers made by Sympatex Technologies. The wicking material can be laminated to the water vapor breathable medium to form a composite material.

The arrangement of flow spaces which are bounded by the cover structure 610 provides a relatively large surface area of the inner layer of water wicking material in the cover structure 610 which bounds a substantial part of the inner flow space 625. In one embodiment of the present invention, the surface area of the cover structure 610 can vary in a range from 120 to 160 square inches, but can also be at least 80 to 100 square inches. While the size of the cover structure 610 and overall device 600 is limited by the need for a reduced compliance when connected to a breathing circuit, it understood that the particular size of the present invention can be made to suit the needs of the patient. The arrangement of flow spaces in the present invention also provides a relatively long dwell time for fluid flow through the device 600 from the entry port 604 through to the exit port 606, since the fluid flowing from the entry port 604 is directed furthest away from the entry port 604 to the lower end portion of the device 600 at the lower end 616 of the cover 610, and then back through tube 670 to the exit port 606 to maximize the travel time of fluid flow through the device. Furthermore, the capillary action of the inner layer of water wicking material causes moisture or water vapor to be adsorbed on the inner surface of cover structure 610 and absorbed into the inner layer, which water vapor or moisture then enters the second outer layer of the cover structure 610 which is made of a water vapor breathable material which allows water vapor to flow from within the device 600 out to the surroundings.

The present invention therefore provides a superior way of removal of moisture or water vapor from a breathing circuit, which is better than water traps or other fluid dissipation or moisture removal devices known in the prior art. The superior performance of the present invention is due to a number of factors, including one or more of: (i) the greater surface area of flow spaces 625 bounded by a water vapor breathable medium afforded by the arrangement of the structure of the device 600; (ii) the use of a water wicking material in the inner layer of the cover element 610; and/or (iii) the relatively long dwell times and flow paths through the device 600 from the entry port 604 to the exit port 606. The result of the inventive apparatus disclosed is that when device 600 is connected to a breathing circuit, rainout or condensation in the breathing tube and collection of water within the breathing circuit is significantly reduced.

Figure 22:
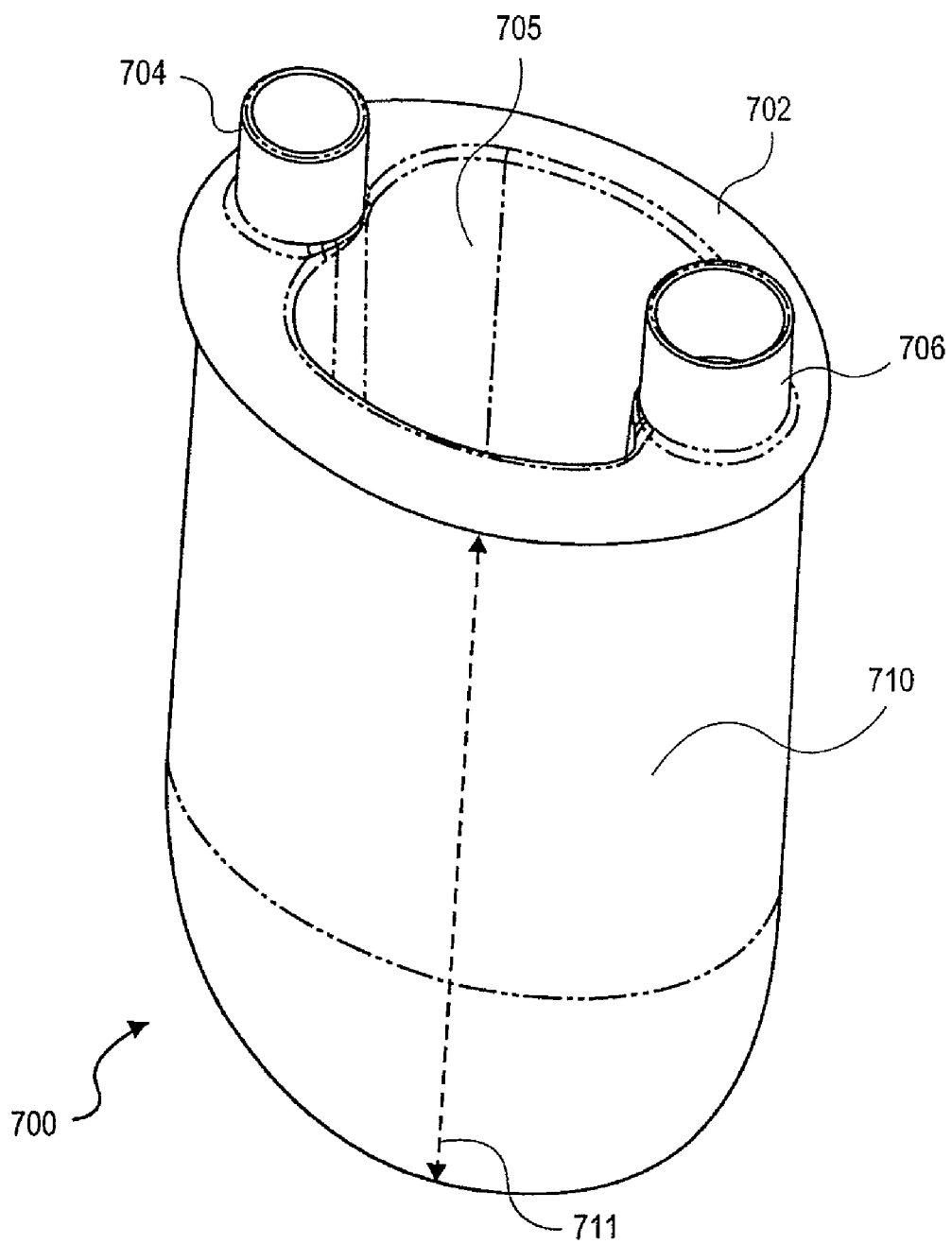
FIG. 22 is an illustration of a water dissipation device according to one or more embodiments of the invention.

FIG. 22 is an illustration of a water dissipation device according to one or more additional embodiments of the invention, as more fully explained below. The device 700 can include two ports 704 and 706 extending from an upper lid portion 702. The ports 704 and 706 can be coupled to a breathing circuit and can be entry or exit ports for flow to enter and exit from the breathing circuit. An outer cover structure 710 extends from the upper lid structure and is generally bucket or cup shaped, as explained more fully herein. In the device shown in FIG. 22, the device is fully assembled and can be representative of the basic features of the embodiments discussed further herein. In particular, the device 700 shows that the outer cover structure 710 extends for a depth 711 from the upper lid portion 702, and has a bucket or cup-shaped configuration 705 that encloses a volume inside. The device 700 therefore provides in inner flow space between the entry and exit ports bounded and enclosed by combination of the outer cover structure 710, upper lid portion 702 and its bucket of cup-shaped configuration extending into the volume enclosed by the outer cover structure. In this inner flow space, breathing gases containing water vapor or moisture can circulate and allow for such water vapor and moisture to collect inside in liquid form, similar to a water trap. The present invention provides an outer cover structure 710 which is made of at least two layers, including an first, inner layer made of water or moisture wicking material, and second, outer layer made of a water vapor breathable material. The first layer of wicking material adsorbs and/or absorbs water or moisture inside the device 700 which have circulated or condensed inside its inner flow space and in contact with the inner surface area of the outer cover structure 710. The capillary action provided by the wicking material draws water or moisture from one region of the outer cover structure 710 to another region of the outer cover structure 710 and thus enables a greater surface area of the outer cover structure 710 to collect, absorb, and transfer water vapor or condensate. After permeating through the first inner layer of wicking material, the water vapor or moisture can then diffuse or transfer by osmosis through the second layer of the outer cover structure 710 which is made of a material that transfers only water vapor, as is well known in the art, and explained in more detail herein. Thus the device 700 provides an inner flow space and contact surface area bounded and enclosed by the outer cover structure 710 made of at least the two layers discussed herein, which enables water vapor or moisture to dissipate from the breathing circuit flow to which the device is connected out to the surroundings. This effectively and automatically removes water vapor and condensate from a breathing circuit which is novel and inventive over all known devices in this field.

Figure 23:
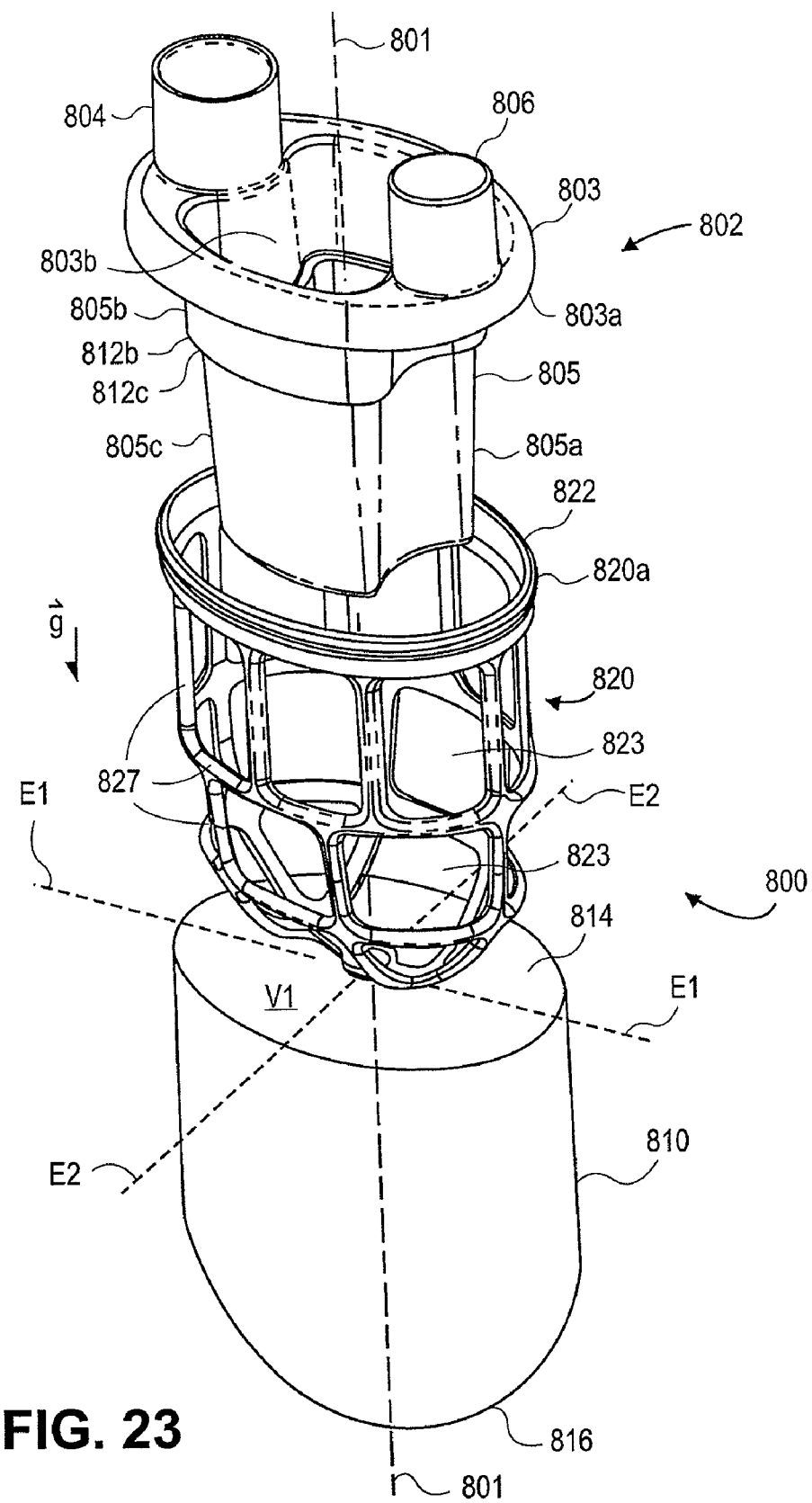
FIG. 23 is an exploded view illustrating a water dissipation device according to an embodiment of the invention.

FIG. 23 is an exploded view illustrating a water dissipation device according to an exemplary embodiment of the invention. The device 800 shown in FIG. 23 can be a smaller version of the inventive device suited more particularly for application with pediatric patients, and is similar in assembled form in certain respects to the features of the device 700 shown in FIG. 22. As shown in FIG. 23, the device 800 has three main components which have been exploded in the view of FIG. 23 along a depth axis 801 extending along the center of the device from an upper end to a lower end of the device 800. The device 800 is preferably oriented such that its depth axis 801 is aligned with the direction of gravity, shown by gravity vector "g" in FIG. 23, although deviations from this orientation or different alignments are possible.

Figure 24:
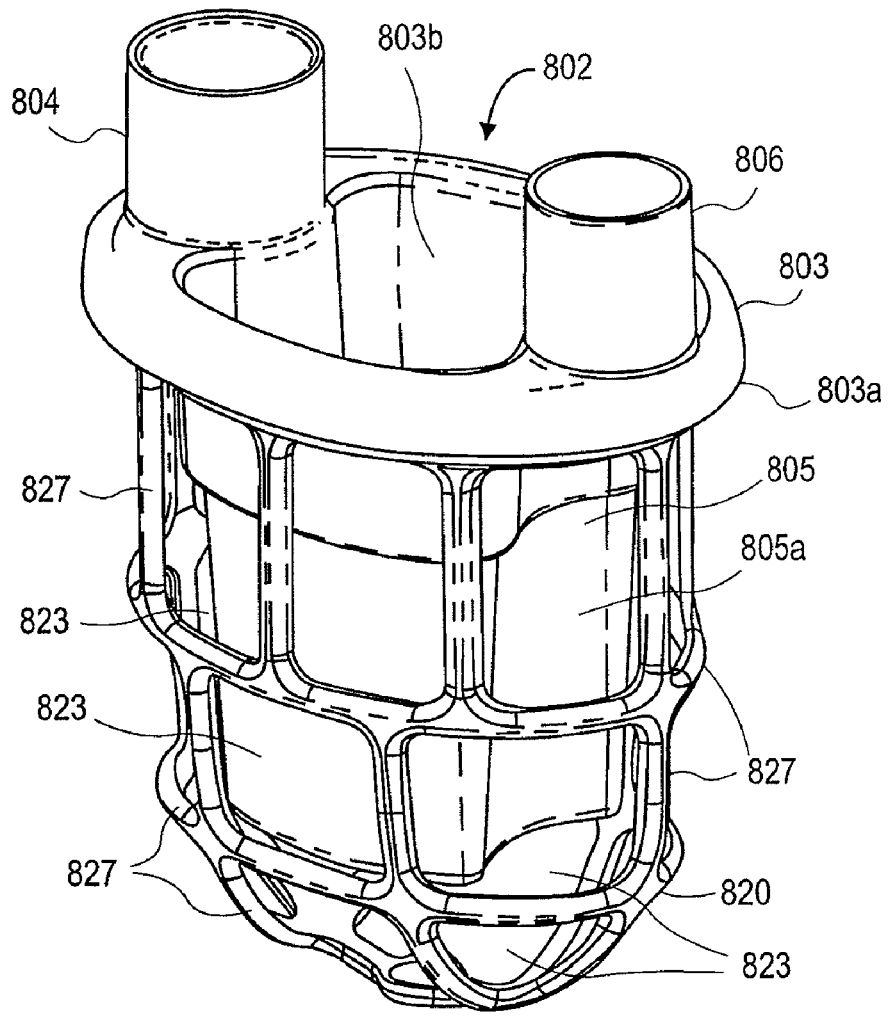
FIG. 24 is a view illustrating the water dissipation device of FIG. 23, in assembled form but without an outer cover structure.

The components of the device 800 include a lid and inner cup assembly 802, an outer cover structure 810, and an inner frame 820. As shown in FIG. 23, inner frame 820 fits inside outer cover structure 810 through a mouth or upper top opening 814 defined by the outer cover structure 810, and lid and inner cup assembly 802 fits on top of an upper mouth or top opening 822 of the inner frame 820, with an inner cup structure portion 805 fitting through said opening 822 to be enclosed by the inner frame 820 when the device is fully assembled. As shown in FIGS. 23 and 24, the inner frame 820 can be a truss-like structure having a bucket-shaped or cup-shaped configuration and can be made up of a series of interconnected span or strut elements 827 which also define a plurality of windows, spaces or openings 823 between the various span or strut elements 827. The lid and inner cup assembly includes at least an upper lid portion 803, an entry port 804 and an exit port 806 as best shown in FIG. 23. The inner cup structure 805 extends from the upper lid portion 803 as a bucket or cup-shaped structure into a volume circumscribed or enclosed by the inner frame and outer cover structure when the device 800 is in fully assembled form, described in more detail below.

Figure 25:
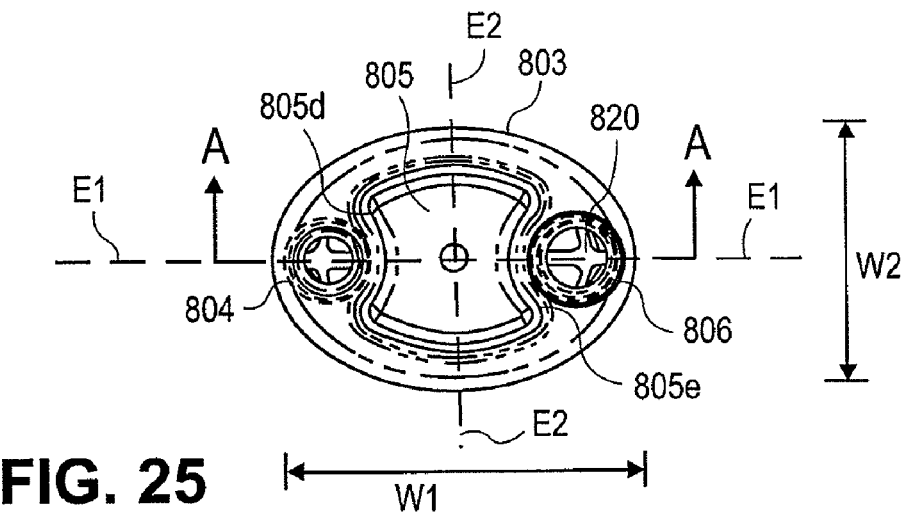
FIG. 25 is a top view of the water dissipation device of FIG. 23.

FIG. 24 is a view illustrating the water dissipation device 800 of FIG. 23, in assembled form but without the outer cover structure 810, showing how the lid and inner cup assembly 802 and in particular the inner cup structure 805 fits inside the inner frame 820. The lid and inner cup assembly 802 thus has an upper lid portion 803 which is a kind of lid or cap having an outer rim 803a which has a circumferential perimeter which envelops or fits around the upper circumferential edge or perimeter 820a of the inner frame 820 as shown in FIGS. 23 and/or 24. The center area 803b enclosed by the inner cup structure 805 of the upper lid portion 803 is hollowed out defining a space or volume which extends downwards along axis 801 as an inner volume enclosed by the inner cup structure 805 having sidewalls 805a which extend downwards from the outer rim 803a. Outer rim 803a further defines a lip or overhang which fits over the circumferential perimeter 820a of inner frame 820. FIG. 25 is a top view of the water dissipation device of FIG. 23.

Figure 25A:
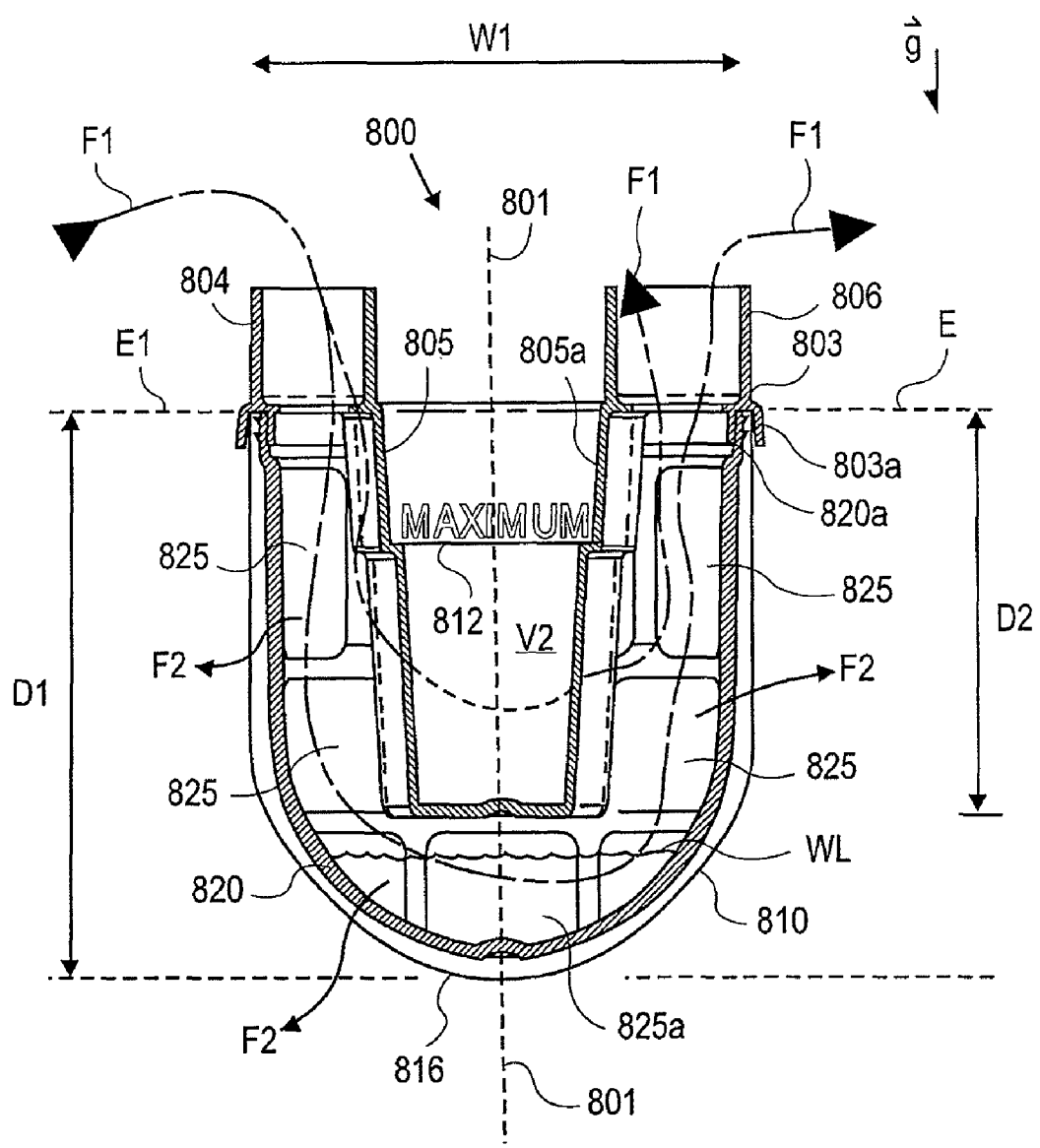
FIG. 25A is a cross-sectional view of the water dissipation device of FIG. 23 taken along section A-A in FIG. 25.

FIG. 25 is a top view of the water dissipation device of FIG. 23, showing the contours and features of parts of the inner cup structure 805 in outline. FIG. 25A is a cross-sectional view of the water dissipation device of FIG. 23 taken along section A-A in FIG. 25. As shown in FIG. 25, the cross-sectional shape of the inner cup structure 805 transverse to the depth axis of the device is not circular and instead includes at least two curved sidewalls 805d and 805e which partially define a channel or flow pathway directly below the entry and exit ports 804 and 806 respectively, which flow pathways extend through said ports through the upper lid portion 803 and into an inner flow space inside the device 800 bounded by the upper lid portion 803, inner cup structure 805, and outer cover structure 810, when the device 800 is fully assembled as shown in FIG. 25A. The inner flow space is further bounded by the structure of the inner frame 820 in that any flow inside the flow space must flow around the spans and struts of the frame 820.

As shown in FIGS. 23 and/or 25, the device 800 defines a cross-sectional shape transverse to the depth that can be elliptical and non-circular. In FIG. 23 there is shown two axes E1 and E2, which span the width of the device 800 and its components along a plane transverse to and normal with depth axis 801, shown as transverse plane "E" in FIG. 25A. In the embodiment shown in FIG. 23, where the cross-sectional shape of the device 800 can be approximated as an ellipse, axis E1 and axis E2 can be aligned with the major and minor axes, respectively, of the ellipse approximated by said cross-sectional shape. As shown in FIG. 25 and FIG. 25A, the width of the device 800 and its outer cover structure 810 can be approximated as a first width "W1" along axis E1, and as a second width "W2" along axis E2, which widths can be the widths of the elliptical span of the transverse cross-section of the top opening 814 of the outer cover structure 810 along the major and minor axes of said elliptical span. Furthermore, as shown in FIG. 25A, the depth of the device 800 and its outer cover structure 810 can be approximated as a depth "D1" extending from transverse plane "E" along depth axis 801, which transverse plane is coincident with the upper end and upper top opening 814 of the outer cover structure 810 as well as the approximate level where outer rim 820a of inner frame 820 mates with the lip or outer rim 803a of the upper lid portion 803.

Accordingly, the embodiment of the invention shown in FIGS. 23-25A includes a water dissipation device for removing water vapor or moisture from a breathing circuit. The device 800 includes an upper lid portion 803, an entry port 804 for receiving flow from a breathing circuit, and an exit port 806 for flow exiting the device 800. The outer cover structure 810 extends from the upper lid portion 803 to define an enclosed volume V1 bounded by the surface area of the outer cover structure 810 and the elliptical span of the transverse cross-section of top opening 814, as shown in FIG. 23 and having a depth D1 as shown in FIG. 25A between the upper lid portion and a lower or bottom end portion 816 of the device 800. In the embodiment shown in FIGS. 23-25A, the lower or bottom end portion 816 of the device also is the lower or bottom end of the outer cover structure 810, since such outer cover structure is a bucket or cup-shaped structure which encloses and covers the lower or bottom end of the enclosed volume V1 and inner frame 820 which fits inside said volume V1. Enclosed volume V1 therefore is a space or volume bounded by an inner surface of the outer cover structure 820 and the upper transverse plane "E" proximate the upper lid portion 803. The inner frame 820 extends from the upper lid portion 803 inside the outer cover structure 810 into enclosed volume V1, such that the device 800 defines a complex inner flow space inside the enclosed volume V1 at least for fluid flow from the entry point 804 through the inside of the device 800 and eventually to the exit port 806. It will be appreciated that the entry and exit ports could be reversed such that the entry port is 806 and the exit port is 804, since flow inside the inner flow space in enclosed volume V1 could easily flow either way between said ports, depending on which way the device 800 is coupled to a breathing circuit.

The inner flow space defined inside device 800 is shown in FIG. 25A as a number of spaces 825 which are bounded by the configuration of the outer cover structure 810, inner cup structure 805 and in particular its sidewalls 805a, and the upper lid portion 803 and the span of entry and exit ports 804 and 806 along transverse plane E. The inner flow space 825 is further bounded by the structure of the inner frame 820 in that the inner frame 820 displaces some of the volume inside the enclosed volume inside the outer cover structure 810 and so any flow inside the flow space 825 must flow around the spans and struts of the frame 820. In FIG. 25A, the flow of breathing gases or fluid from a breathing circuit coupled to entry port 804 is shown as directional pathways F1, which flow first enters the device 800 through the entry port 804 and then passes transverse top plane "E" and enters the enclosed volume inside the outer cover structure 810 and into the inner flow space 825 therein. However, because inner cup structure 805 extends from the upper lid portion 803 into the enclosed volume, the flow along F1 inside a portion of the inner flow space is bounded by the sidewalls 805a of the inner cup structure 805 which displaces a significant portion of the enclosed volume, such that the flow is urged and directed to flow first towards the lower or bottom end 816 of the device 800, into the portion 825a of the inner flow space 825 proximate to bottom end 816, before returning though another portion of the inner flow space 825 up past again the sidewalls 805a of the inner cup 805 and to through to the exit port 806.

Thus the device 800 directs the flow F1 to tend to flow from the upper end of the device 800 near top plane "E" down to the lower end 816 first before exiting the device, such that the travel and dwell time of flow inside the device is lengthened or maximized. This causes the flow F1 inside flow space 825 to have greater contact with the inner surface area of outer cover structure 810. This lengthening of the travel and dwell time, and increase of contact with the inner surface area of the outer cover structure 810 enhances the water dissipation function of the device, as explained more fully below.

To enable the dissipation of water vapor or moisture through the device 800 from flow supplied from a breathing circuit to which the device is connected, the outer cover structure 810 of water dissipation device 800 includes at least a first layer of water or moisture wicking material and a second layer of water vapor breathable medium over the first layer. The first layer of water or moisture wicking material is what forms the inner surface area of the outer cover structure 810 which bounds at least a portion of the inner flow space 825 such that water vapor or moisture can permeate from the inner flow space 825 through the outer cover structure 810 and out of device 800, as shown by a few exemplary directional flow indicators "F2" as shown in FIG. 25A. It will be appreciated however, that the dissipation of water vapor or moisture can take place across the entire surface span of outer cover structure 810 which bounds the inner flow space 825 and is exposed on its outer surface to the atmosphere or surroundings. If the concentration of water vapor or moisture inside the inner flow space 825 and/or the breathing gases or fluids flowing therein is higher than the concentration of water vapor or moisture outside the device 800, then water vapor or moisture will tend to travel through capillary action, osmosis, and/or other modes into first the first layer of water and/or moisture wicking material, and then through the second layer of water vapor breathable material, such that water vapor effectively exits the device 800 along a pathway other than through the exit port 806. The present invention therefore allows for water vapor or moisture to be effectively and automatically removed from high humidity or water vapor or moisture containing breathing gases flowing from breathing circuits to which the device 800 is connected or coupled.

Another advantage of the present invention as shown in the embodiment in FIGS. 23-25A is that the inner cup structure 805 extends into the enclosed volume to displace a displacement volume V2 inside the enclosed volume to define a compressible volume defined by and within the inner flow space inside the device. Generally, in breathing circuit applications, it is important to minimize the compressible volume inside a device to make breathing easier and more efficient for a patient, as is well known in the art. In the embodiment shown in FIG. 25A, it can be seen that the inner cup structure 805 extends for a span "D2" of at least half the depth "D1" into the enclosed volume. Therefore, the inner cup structure 805 extends significantly into the enclosed volume to create a compressible volume which is significantly less than it would otherwise be had the inner flow space taken up nearly the entire enclosed volume V1. In one example of embodiment of the present invention, the depth D1 can be approximately four inches, depth D2 can be approximately three inches, while width W1 can be approximately 3.5 inches, and width W2 can be approximately 2.5 inches, such that the compressible volume inside the inner flow space can be up to approximately 50% less than the enclosed volume. Furthermore, in such example of such an embodiment, the inner surface area of the outer cover structure can be approximately 45 square inches, such that the ratio of the inner surface area of the outer cover structure over the depth D1 is about 11.25, but, given that the device can be made in varying dimensions and particular ranges of depths D1, D2 and widths W1 and W2, such ratio of the inner surface area of the outer cover structure over the depth can be in the range of 10 to 12.50.

When the device 800 is coupled to a breathing circuit, often the water vapor and moisture content is so high that moisture condenses inside the device inside flow space 825 to collect as a pool of water at the bottom of the outer cover structure 816, shown by an example water level "WL" in FIG. 25A. If the water level WL were to get too high up depth axis 801, it could occlude the flow through the device between the entry and exit ports 804 and 806. To enable monitoring of this possibility, as shown in FIG. 25A, the inner cup structure 805 includes a sidewall 805a providing a visual water level indicator 812 calibrated to indicate the maximum level of water condensate pooling inside the device for safe operation. As best shown in FIG. 23, visual water level indicator is provided by the sidewall 805a having a first upper sidewall portion 805b having a lower end 812b and a second lower sidewall portion 805c having an upper end 812c, the lower end 812b of the upper portion 805b having a first width and the upper end 812c of the lower portion 805c having a second width different from the first width. Thus the sidewalls 805a of the inner cup structure 805 have a stepped configuration where the width of the walls discontinuously changes at a certain level which is determined and/or calibrated to be a maximum level for safe operation of the device. If water were to collect inside device 800 up to the level 812, a user viewing inside the inner cup structure 805 from the top of the device into inner displacement volume V2 defined by the inner cup 805 (as shown in FIG. 25A) can more easily and prominently notice the water level about stepped width at level 812 and therefore determine that the maximum water level has been met or exceeded.

The present invention as shown in the embodiment and examples with regard to FIGS. 23-25A is also advantageous over prior water traps known by those of skill in the art because the inner cup structure 805 extends into the enclosed volume V1, and flow through the device 800 is lengthened in dwell time inside the device and concurrently has increased contact with the inner surface area and inner wicking layer of outer cover structure 810, such that the water vapor or moisture in the flow through the device is drawn by the increased surface area contact of the wicking layer, and the capillary action it enables, such that water vapor or moisture is absorbed and/or adsorbed to a greater extent across the full span and surface area of the wicking layer and thus transfers through the outer cover structure overall so that a greater amount of water vapor or moisture can be dissipated by the device. As shown in FIG. 25A, water condensed in a pool at the bottom end of the device 800 can be absorbed by the inner wicking layer in outer cover structure 810 and thus be drawn up into the portion of the outer cover structure 810 above water level WL, such that a greater amount of water vapor or moisture permeates through the outer cover structure 810 through the second, outer layer of water-vapor breathable medium in contact with the first layer of wicking material, and thus dissipates out of the device 800 and out of the breathing circuit to which the device is connected or coupled.

Figure 26:
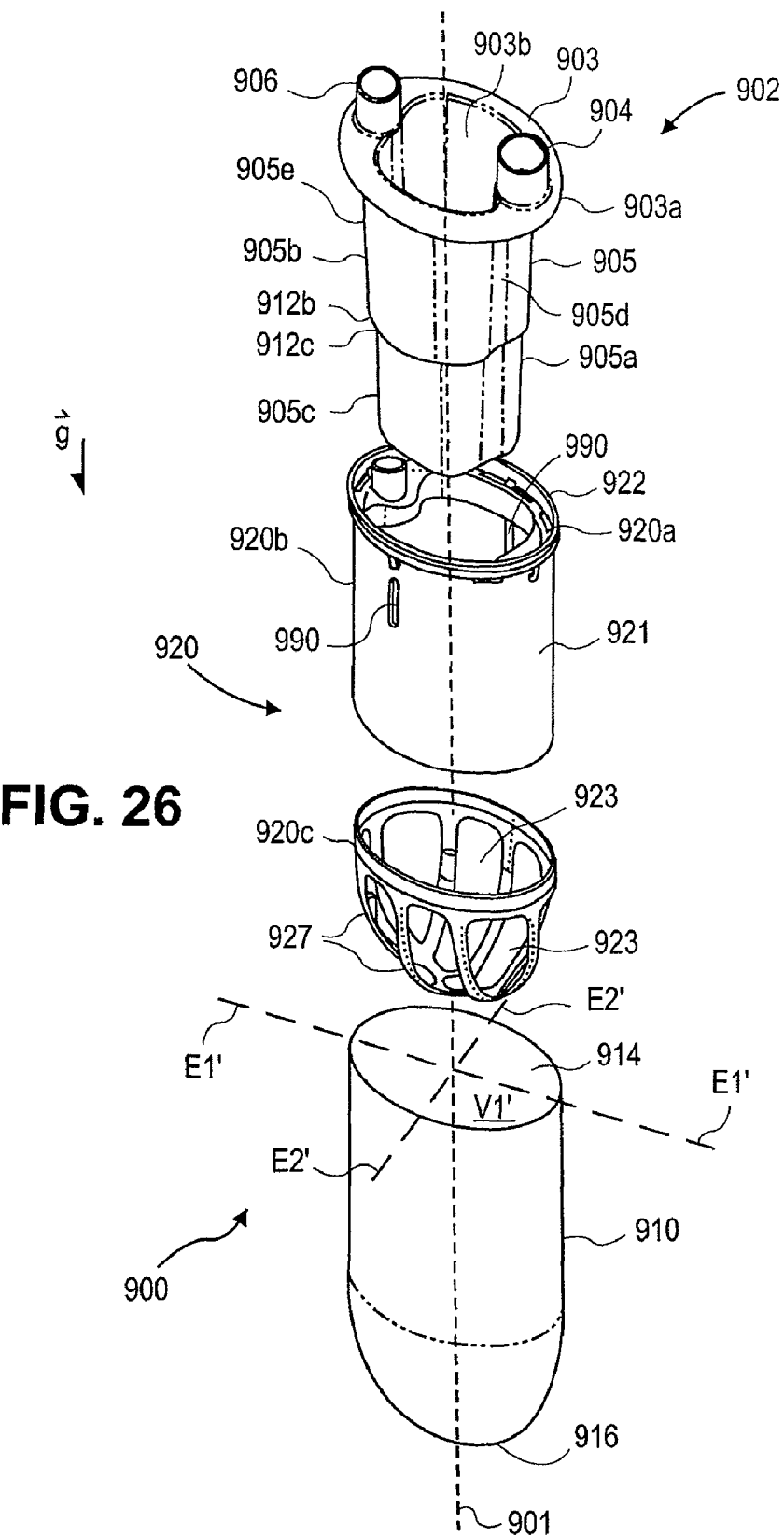
FIG. 26 is an exploded view illustrating a water dissipation device according to another embodiment of the invention.

FIG. 26 is an exploded view illustrating a water dissipation device according to another exemplary embodiment of the invention. The device 900 shown in FIG. 26 can be a larger version of the inventive device suited more particularly for application with adult patients, and is similar in assembled form in certain respects to the features of the device 700 shown in FIG. 22. As shown in FIG. 26, the device 900 has three main components which have been exploded in the view of FIG. 26 along a depth axis 901 extending along the center of the device from an upper end to a lower end of the device 900. The device 900 is preferably oriented such that its depth axis 901 is aligned with the direction of gravity, shown by gravity vector "g" in FIG. 26, although deviations from this orientation or different alignments are possible.

The components of the device 900 include a lid and inner cup assembly 902, an outer cover structure 910, and an inner frame 920 which can have an upper frame portion 920b and a lower frame portion 920c. The upper frame portion 920b can be integrally made with lower frame portion 920c as a single piece or can be two pieces attached or bonded together. The exploded view of FIG. 26 shows the two pieces 920b and 920c as separate for ease of viewing and explanation herein. As shown in FIG. 26, inner frame 920 fits inside outer cover structure 910 through a mouth or upper top opening 914 defined by the outer cover structure 910, and lid and inner cup assembly 902 fits on top of the upper mouth or top opening 922 of the inner frame, with an inner cup structure portion 905 fitting through said opening 922 to be enclosed by the inner frame 920 when the device is fully assembled. As shown in FIG. 26, the lower inner frame portion 920c can be a caged or truss-like structure having a bucket-shaped or cup-shaped configuration and can be made up of a series of interconnected span or strut elements 927 which also define a plurality of windows or openings 923 between the various span or strut elements 927. The lid and inner cup assembly 902 includes at least an upper lid portion 903, an entry port 904 and an exit port 906 as shown in FIG. 26. The inner cup structure 905 extends from the upper lid portion 903 as a bucket or cup-shaped structure into a volume circumscribed or enclosed by the inner frame 920 and/or outer cover structure 910 when the device 900 is in fully assembled form, described in more detail below.

FIG. 27 is a view illustrating the water dissipation device 900 of FIG. 26, in assembled form but without an outer cover structure 910, showing how the lid and inner cup assembly 902 and in particular the inner cup structure 905 fits inside the inner frame 920. FIG. 28 is a view illustrating the inner frame structure 920 of the water dissipation device 900 of FIG. 26. The lid and inner cup assembly 902 thus has an upper lid portion 903 which is a kind of lid or cap having an outer rim 903a which has a circumferential perimeter which envelops or fits around the upper circumferential edge or perimeter 920a of the inner frame 920. The center area 903b enclosed by inner cup structure 905 and bounded at its top end by the outer rim or perimeter 903a of the upper lid portion 903 is hollowed out defining a space which extends downwards along axis 901 as an inner volume enclosed by the inner cup structure 905 having sidewalls 905a which extend downwards from the outer rim 903a. Thus outer rim 903a defines a lip or overhang which fits over the circumferential perimeter 920a of inner frame 920.

As shown in FIGS. 26-28, the inner frame upper portion 920b includes a substantially cylindrical annular wall portion 921 which extends from the upper lid portion 903 when the device 900 is fully assembled. In the example of the embodiment of the invention shown in FIGS. 26-28, the extent of the annular wall portion 921 is that it has a depth which is at least one half of the depth of the overall device 900 and the outer cover structure 910 as explained more fully herein. The annular wall portion 921 therefore defines a smooth cylindrical surface, which cylinder can have a non-circular cross-section, and which surface forms a substantial portion of the exterior surface of the upper portion 920b of inner frame 920. When the device 900 is fully assembled, outer cover structure 910 narrowly surrounds the annular wall portion 921 of the inner frame to define a narrow annular flow space therebetween, the annular flow space being a portion of the inner flow space inside the device 900 and in fluid communication with the entry port 904.

Figure 30:
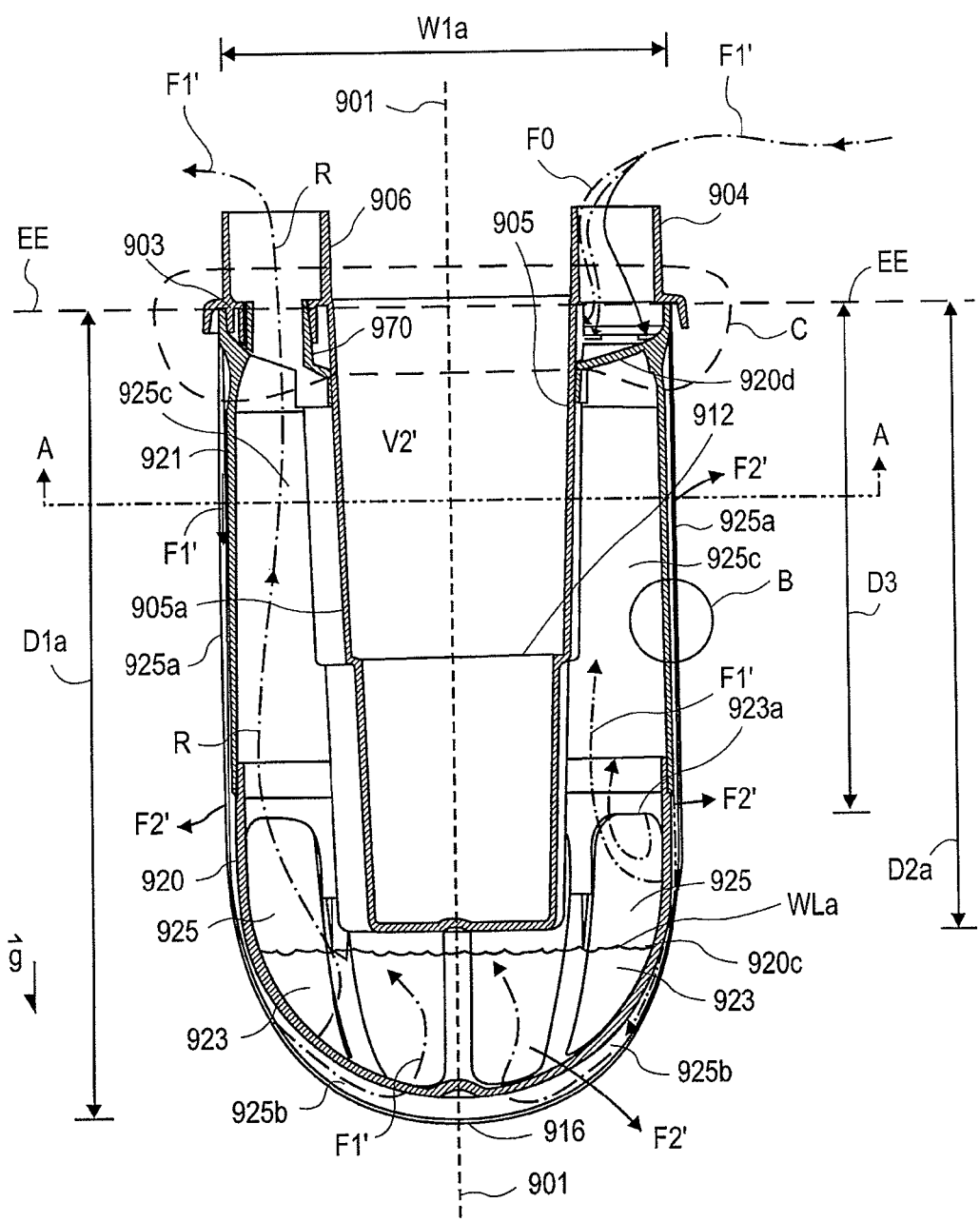
FIG. 30 is a cross-sectional view of the water dissipation device of FIG. 26 in assembled form taken along section X-X in FIG. 29.

FIG. 29 is a top view of the water dissipation device 900 of FIG. 26, showing the contours and features of parts of the inner cup structure 905 in outline. FIG. 30 is a cross-sectional view of the water dissipation device 900 of FIGS. 26 and 29 in assembled form taken along section X-X in FIG. 29. As shown in FIG. 29, the cross-sectional shape of the inner cup structure 905 transverse to the depth axis is not circular and instead includes at least two curved sidewalls 905d and 905e which partially define a channel or flow pathway directly below the entry and exit ports 904 and 906 respectively, which flow pathways extend through said ports through the upper lid portion 903 and into an inner flow space inside the device 900 bounded by the upper lid portion 903, inner cup structure 905, and outer cover structure 910, when the device 900 is fully assembled as shown in FIG. 30. The inner flow space is further bounded by the structure of the inner frame 920 in that any flow inside the flow space must flow around the structure of the frame 920.

As shown in FIGS. 26 and/or 29, the device 800 defines a cross-sectional shape transverse to the depth that can be elliptical and non-circular. In FIGS. 26 and 29 there is shown two axes E1' and E2', which span the width of the device 900 and its components along a plane transverse to and normal with depth axis 901, shown as transverse plane "EE" in FIG. 30. In the embodiment shown in FIG. 26, where the cross-sectional shape of the device 900 can be approximated as an ellipse, axis E1' and axis E2' can be aligned with the major and minor axes, respectively, of the ellipse approximated by said cross-sectional shape. As shown in FIG. 29 and FIG. 30, the width of the device 900 and its outer cover structure 910 can be approximated as a first width "W1a" along axis E1, and as a second width "W2a" along axis E2, which widths can be the widths of the elliptical span of the transverse cross-section of the top opening 914 of the outer cover structure 910 along the major and minor axes of said elliptical span. Furthermore, as shown in FIG. 30, the depth of the device 900 and its outer cover structure 910 can be approximated as a depth "D1a" extending from transverse plane "EE" along depth axis 901, which transverse plane is coincident with the upper end and upper top opening 914 of the outer cover structure 910 as well as the approximate level where outer rim 920a of inner frame 920 mates with the lip or outer rim 903a of the upper lid portion 903.

Accordingly, the embodiment of the invention shown in FIGS. 26-30 includes a water dissipation device for removing water vapor or moisture from a breathing circuit. The device 900 includes an upper lid portion 903, an entry port 904 for receiving flow from a breathing circuit, and an exit port 906 for flow exiting the device 800. The outer cover structure 910 extends from the upper lid portion 903 to define an enclosed volume V1' bounded by the surface area of the outer cover structure 910 and the elliptical span of the transverse cross-section of top opening 914 as shown in FIG. 26 and having a depth D1a as shown in FIG. 30 between the upper lid portion 903 and a lower or bottom end portion 916 of the device 900. In the embodiment shown in FIGS. 26-30, the lower or bottom end portion 916 of the device also is the lower or bottom end of the outer cover structure 910, since such outer cover structure is a bucket or cup-shaped structure which encloses and covers the lower or bottom end of the enclosed volume V1' and inner frame 920 which fits inside said volume V1'. Enclosed volume V1' therefore is a space or volume bounded by an inner surface of the outer cover structure 920 and the upper transverse plane "EE" proximate the upper lid portion 903. As shown in FIG. 30, the inner frame 920 having a substantially cylindrical annular wall portion 921 extends from the upper lid portion 903 inside the outer cover structure 910 into enclosed volume V1', such that the device 900 defines an inner flow space inside the enclosed volume V1' at least for fluid flow from the entry port 904 through the inside of the device 900 to the exit port 906. It will be appreciated that the entry and exit ports could be reversed such that the entry port is 906 and the exit port is 904, since flow inside the inner flow space in enclosed volume V1' could potentially flow either way between said ports, depending on which way the device 900 is coupled to a breathing circuit.

The inner flow space defined inside device 900 is shown in FIG. 30 as a number of spaces 925 which includes flow spaces 925a and 925b, which overall are bounded by the configuration of the outer cover structure 910, inner cup structure 905 and in particular its sidewalls 905a, and the upper lid portion 903 and its entry and exit ports 904 and 906 spanning transverse plane EE. The inner flow space 925 is further bounded by the structure of the inner frame 920 in that the inner frame 920 displaces some of the volume inside the enclosed volume inside the outer cover structure 910 and so any flow inside the flow space 925 must flow around the spans and struts of the frame 920. In FIG. 30, the flow of breathing gases or fluid from a breathing circuit coupled to entry port 904 is shown as directional pathways F1', which flow first enters the device 900 through the entry port 904 and then passes transverse top plane "EE" and enters the enclosed volume inside the outer cover structure 910 and into the inner flow space 925 therein.

Figures 31A, 31B, 31C:
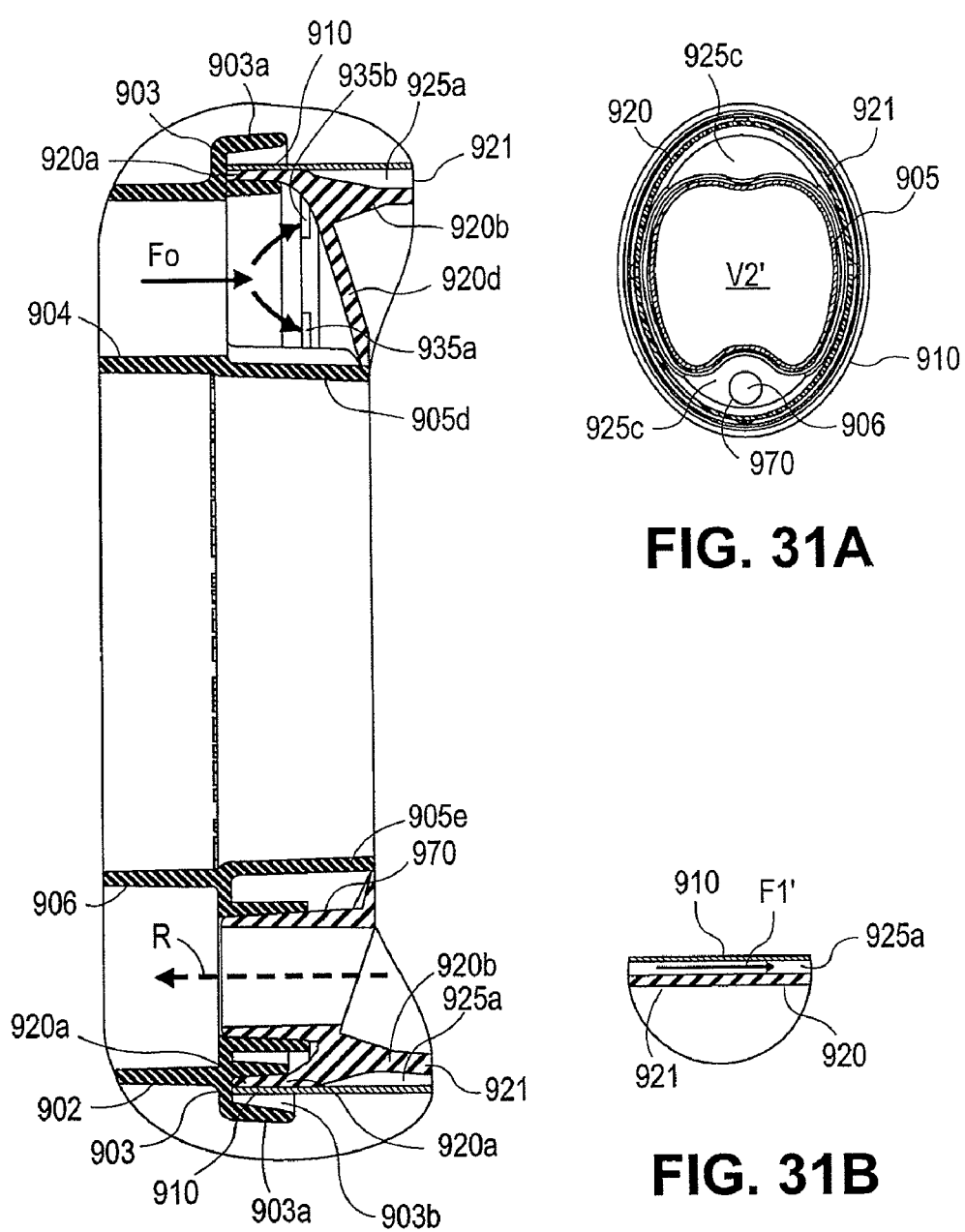
FIG. 31A is a cross-sectional view of a portion of the water dissipation device taken along section A-A in FIG. 30.
FIG. 31B is a detailed view of a portion of the water dissipation device shown in FIG. 30 in region "B" therein.
FIG. 31C is a detailed view of a portion of the water dissipation device shown in FIG. 30 in region "C" therein.

In the embodiment shown in FIGS. 26-30, the inner flow space 925 is also defined at least in part by the outer cover structure 910 which narrowly surrounds the annular wall portion 921 of the inner frame 920 to define a narrow annular flow space 925a therebetween, the annular flow space 925a being a portion of the inner flow space 925 and in fluid communication with the entry port 904, which is between the outer cover structure 910 and the annular wall portion 921 of the inner frame 920 when the device 900 is fully assembled, as best shown in FIG. 30. FIG. 31B is a detailed view of a portion of the water dissipation device shown 900 in FIG. 30 in region "B" therein, showing a portion of the narrow annular flow space 925a between a portion of the outer cover structure 910 and annular wall portion 921 of inner frame 920, with flow F1' flowing therethrough.

As best illustrated in FIG. 28, the flow entering the device 900 from entry port 904 is evenly distributed into and around the circumference of the annular flow space 925a by a circumferential array of flow vents 935 disposed along a circumference inside the outer rim of 920a through the structure of the inner frame 920. As best shown in FIGS. 26 and 29, the inner cup structure 905 has a transverse cross-sectional shape that is non-circular and includes two curved sidewall portions 905d and 905e which mate with correspondingly curved flanges 941 and 942, respectively, extending from the inner frame 920 inside an inner wall 945 of said upper portion of said frame 920, radially just inside the array of flow vents 935, as shown in FIG. 28. FIG. 31C is a detailed view of a portion of the water dissipation device shown in FIG. 30 in region "C" therein, showing how the outer rim 903a of the upper lid portion 903 mates over the upper rim 920a of the inner frame 920. Circumferential lip 903a defines an inner annular space 903b into which an upper flange of upper rim 920a and the upper end of outer cover structure 910 are disposed. When the lid and inner cup assembly 902 is positioned on top of and inside the inner frame 920 when the device 900 is fully assembled, the mating of: (i) an upper portion of curved sidewall 905d with curved flange 941, and (ii) an upper portion of curved sidewall 905e with curved flange 942, and (iii) the upper portion of the rest of sidewall 905a with inner wall 945, and (iv) the upper lid 903 over the upper rim 920a of inner frame 920, causes initial flow "F0" entering the device through entry port 904 to be distributed to the array of flow vents 935 around the periphery of the inner frame upper portion radially just inside the outer rim 920a, such as vent openings 935a and 935b shown in FIG. 31C, and flows therethrough into the annular flow space 925a circumferentially around the annular wall portion 921. Distribution of the flow through vents 935 circumferentially around the periphery of the device 900 into annular flow space 925a promotes greater contact with the media in the outer cover structure, as explained more fully below, and creates greater potential for cooling and condensation inside the device, thus enabling greater moisture removal. Thus, the device 900 defines a plurality of flow paths from the entry port 904 to the annular flow space portion 925a of the inner flow space 925 inside device 900. The flow therefore proceeds along the relatively thin annular flow space 925a which is bounded by the outer cover structure 910 and annular wall portion 921 and provides a significant surface area which is in direct contact with the flow inside a relatively small annular volume in flow space 925a, which thereby enhances the effect of water vapor and moisture absorption and adsorption by the layers comprising the outer cover structure 910 as discussed more fully herein. In the example of the embodiment in FIG. 30, the annular flow space 925a extends to the depth D3 as shown, which depth D3 is marked by the uppermost extent 923a of windows or openings 923 defined by the lower portion 920c of inner frame 920, and which depth D3 is at least half the depth D1a of the overall device 900.

Because the annular flow space 925a can extend for a depth D3 below the top transverse plane EE and entry port 904, and because inner cup structure 905 extends from the upper lid portion 903 into the enclosed volume V1', the flow along F1 inside the inner flow space of the device 900 is urged and directed to flow first through the annular flow space 925a as discussed herein, which directs the flow thereafter towards the lower or bottom end 916 of the device 900, into the portion 925b of the inner flow space 925 proximate to the lower end 916, before returning though a return flow path inside the inner flow space 925 and at least partially surrounded by the annular wall portion 921, said return flow path providing a flow pathway from the annular flow space 925a and out to the exit port 906. As shown in FIG. 30, the lower frame portion 920c of the inner frame 920 extends below the annular wall portion 921, and the outer cover structure 910 covers the lower frame portion to define a closed bottom end 916 of the device. The lower frame portion defines at least one opening 923 though which fluid may flow after exiting from the annular flow space 925a to a return flow path, shown by arrows "R" which form a portion of the flow directions F1' in FIG. 30, which return flow path is at least partially surrounded by the annular wall portion 921. In the embodiment shown in FIGS. 26-30, the lower frame portion 920c is a caged structure defining a plurality of windows 923 each permitting flow from the annular flow space 925a to the rest of the inner flow space 925 and thereby out through return flow path R and to the exit port 906. In the example of the embodiment of the invention shown in FIG. 30, windows 923 extend a level 923a from the closed bottom end 916 of the device up a span equal to about one third of the depth D1a.

FIG. 31A is a cross-sectional view of a portion of the water dissipation device 900 taken along section A-A in FIG. 30. In FIG. 31A, it can be seen that return inner flow path portions 925c of the inner flow space 925 are defined between the walls of the inner cup structure 905 and the annular wall portion 921 of inner frame 920. Thus the return flow R labeled in FIG. 30 as part of the flow paths F1' inside the inner flow space 925 inside the device 900 flows through these spaces 925c which are enclosed by the annular wall 920. The upper portion 920b of inner frame 920 further defines a baffle or upper wall portion 920d, as shown in FIGS. 28, 30, and 31c which blocks the return flow from flow spaces 925c and instead directs the flow to a return port 970 defined by another portion of the upper portion 920b of inner frame 920, as also shown in FIG. 31A, which return port 970 mates with exit port 906, as best shown in FIG. 31C.

Thus the device 900 directs the flow therein to tend to flow from the upper end of the device 900 near top plane "EE" down to the lower end 916 first before exiting the device, such that the travel and dwell time of flow inside the device is lengthened. Furthermore, this causes the flow inside flow space 925 inside device 900 to have greater contact with the inner surface area of outer cover structure 910. This lengthening of the travel and dwell time, and increase of contact with the inner surface area of the outer cover structure 910 enhances the water dissipation function of the device, as explained more fully below.

To enable the dissipation of water vapor or moisture through the device 900 from flow supplied from a breathing circuit to which the device is connected, the outer cover structure 910 of water dissipation device 900 includes at least a first layer of water or moisture wicking material and a second layer of water vapor breathable medium over the first layer. The first layer of water or moisture wicking material is what forms the inner surface area of the outer cover structure 910 which bounds at least a portion of the inner flow space 925 such that water vapor or moisture can permeate from the inner flow space 925, including annular flow space 925a, through the outer cover structure 910 and out of device 900, as shown by a few exemplary directional flow indicators F2' as shown in FIG. 30. It will be appreciated however, that the dissipation of water vapor or moisture can take place across the entire surface span of outer cover structure 910 which bounds the inner flow space 925 and is exposed on its outer surface to the atmosphere or surroundings. If the concentration of water vapor or moisture inside the inner flow space 925a and 925 and/or the breathing gases or fluids flowing therein is higher than the concentration of water vapor or moisture outside the device 900, then water vapor or moisture will tend to travel through capillary action, osmosis, and/or other modes into first the first layer of water vapor and/or moisture wicking material, and then through the second layer of water vapor breathable material, such that water vapor effectively exits the device 900 along a pathway other than through the exit port 906. The present invention therefore allows for water vapor or moisture to be effectively and automatically removed from high humidity or water vapor or moisture containing breathing gases flowing from breathing circuits to which the device 900 is connected or coupled.

Another advantage of the present invention as shown in the embodiment in FIGS. 26-30 is that the inner cup structure 905 extends into the enclosed volume to displace a displacement volume V2' inside the enclosed volume V1' to define a compressible volume defined by and within the inner flow space inside the device. In the embodiment shown in FIG. 30, it can be seen that the inner cup structure 905 extends for a span D2a of at least half the depth D1a into the enclosed volume of the outer cover structure 910. In the example of the embodiment shown in FIG. 30, the span D2a of the depth of the inner cup structure 905 is at least two-thirds of the depth D1a of the overall device. Therefore, the inner cup structure 905 extends significantly into the enclosed volume V1' to create a compressible volume which is significantly less than it would otherwise be had the inner flow space taken up nearly the entire enclosed volume V1'. Furthermore, the non-circular molding profile of the inner cup structure 905 allows for a greater amount of the enclosed volume to be displaced by the inner cup to thereby minimize the compressible volume inside the device. In one example of an embodiment of the present invention, the depth D1$a$ can be approximately eight inches, depth D2$a$ can be approximately six inches, while width W1$a$ can be approximately 4.5 inches, and depth W2 can be approximately 3.25 inches, such that the compressible volume inside the inner flow space can be up to approximately 67% less than the enclosed volume. Furthermore, in such example of such an embodiment, the inner surface area of the outer cover structure 910 can be approximately 100 square inches, such that the ratio of the inner surface area of the outer cover structure over the depth D1 is about 12.50, but, given that the device can be made in varying dimensions and particular ranges of depths D1$a$, D2$a$ and widths W1$a$ and W$a$2, such ratio of the inner surface area of the outer cover structure over the depth can be in the range of 11 to 14.

When the device 900 is coupled to a breathing circuit, often the water vapor and moisture content is so high that moisture condenses inside the device inside flow space 925 to collect as a pool of water at the bottom of the outer cover structure 916, shown by an example water level "WLa" in FIG. 30. If the water level WLa were to get too high up depth axis 901, it could occlude the flow through the device between the entry and exit ports 904 and 906. To enable monitoring of this possibility, as shown in FIG. 30, the inner cup structure 905 includes a sidewall 905$a$ providing a visual water level indicator 912 calibrated to indicate the maximum level of water condensate pooling inside the device for safe operation. As best shown in FIG. 26, visual water level indicator is provided by the sidewall 905$a$ having a first upper sidewall portion 905$b$ having a lower end 912$b$ and a second lower sidewall portion 905$c$ having an upper end 912$c$, the lower end 912$b$ of the upper portion 905$b$ having a first width and the upper end 912$c$ of the lower portion 905$c$ having a second width different from the first width. Thus the sidewalls 905$a$ of the inner cup structure 905 have a stepped configuration where the width of the walls discontinuously changes at a certain level which is determined and/or calibrated to be a maximum level for safe operation of the device. If water were to collect inside device 900 up to the level 912, a user viewing inside the inner cup structure 905 from the top of the device into inner displacement volume V2' defined by the inner cup 905 (as shown in FIG. 30) can more easily and prominently notice the water level about stepped width at level 912 and therefore determine that the maximum water level has been met or exceeded.

The present invention as shown in the embodiment and examples with regard to FIGS. 26-30 is also advantageous over prior water traps known by those of skill in the art because the inner cup structure 905 extends into the enclosed volume V1', and flow through the device 900 is lengthened in dwell time inside the device and concurrently has increased contact with the inner surface area and inner wicking layer of outer cover structure 910, such that the water or moisture in the flow through the device is drawn by the increased surface area contact of the wicking layer, and the capillary action it enables, such that water or moisture is absorbed and/or adsorbed to a greater extent across the full span and surface area of the wicking layer and thus transfers through the outer cover structure overall so that a greater amount of water or moisture can be dissipated by the device. As shown in FIG. 30, water condensed in a pool at the bottom end of the device 900 can be absorbed by the inner wicking layer in outer cover structure 910 and thus be drawn up into the portion of the outer cover structure 910 above water level WLa, such that a greater amount of water vapor or moisture permeates through the outer cover structure 910 through the second, outer layer of water-vapor breathable medium and thus dissipates out of the device 900 and out of the breathing circuit to which the device is connected or coupled.

FIGS. 32A-32C illustrate examples of connector ports or couplings for connecting or coupling the water dissipation device of various embodiments of the invention with a breathing circuit. The connector ports can include vertically orientated 22 mm male and 22 mm female ports such that standard respiratory adaptors may be placed onto the 22 mm female port to adapt to a wide variety of ventilator configurations. Furthermore, the device of the present invention may be coupled to the connectors to allow for swiveling between the connectors and device to allow for greater options with device orientation during operation and/or to facilitate ancillary equipment movement, i.e. water reservoir changes, filter removal, etc. The connectors can include a 90 degree connector as shown in FIG. 32A, for ventilators with a horizontal protruding connection or a 45 degree connector as shown in FIG. 32B. for ventilators with connections protruding downward at a 45 degree angle. Or the connectors can allow the user to add a straight connector for situations when an extension to prevent interference is necessary. The connector can also be vertical as in FIG. 32C, which allows the user to directly attach an external ventilator circuit.

A further feature of the invention as shown in the embodiment of FIGS. 26-30 is the provision of one or more safety openings 990 defined by the annular wall portion 921 of inner frame 920, as shown in FIGS. 26-28, which openings allow flow therethrough if the water level WLa within the device reaches the level 923$a$ at the bottom of the annular wall portion 921. This prevents the almost complete occlusion of flow through the device. The openings 990 are sized small enough such that the majority of flow is directed through the inner flow space 925 as described, starting through the annular flow space 925$a$ and then towards the bottom 916 of the device. It is only when the water level WLa of condensate collects inside the device high enough so that the cage openings 923 of lower frame portion 920$c$ are completely occluded with water, that the openings 990 permit significant flow therethrough. The openings 990 are large enough such that when the entire stream of flow inside the device 900 is directed through the openings 990, the resistance to flow is still small. The total cross-sectional size of the openings can, in the example of the embodiment shown in FIG. 900, be approximately equal to the flow cross-section defined by standard 22 mm diameter connector tubes for coupling with a breathing circuit. As shown in FIG. 26-28, the location of the openings 990 on the annular wall portion 921 is on opposite sides of the annular wall 921, and can be towards the upper portion of the device as to increase the time before the device's inner flow could be completely occluded.

The materials comprising the outer cover structure 810 or 910 and its wicking layer and water vapor breathable layer are water vapor breathable in that both layers allow passage of water vapor. However inner wicking layer is made of wicking material which allows for adsorption and/or absorption of both moisture and water in any phase, gas or liquid, using a capillary action, while the outer layer of water vapor breathable medium permits the passage of water vapor only and not liquid water. Examples of wicking material in the inner layer are a knit or non-woven cloth or fabric, and can be synthetic and made of polyester, polyester and polypropylene blends, nylon, polyethylene or paper, and can be microfilaments or microfiber material such as Evolon® brand fabric material made by Freudenberg & Co. KG. A particular example of wicking material would be a non-woven material of 70% polypropylene and 30% polyester. Another example of the wicking material can be Evolon® brand fabric material having a weight of 60 or 80 grams per square meter. Examples of the outer layer of water vapor breathable medium are Sympatex® brand water vapor permeable membranes made of polymers made by Sympatex Technologies, including monolithic hydrophilic polyester ester membrane, including, as one example, a 12 micron thick membrane. The wicking material can be laminated to the water vapor breathable medium to form a composite laminate material. The lamination can be done using an adhesive, such as a trichloroethylene solvent based urethane adhesive. The adhesive can also be a thermoplastic polyester adhesive bonding at least the first layer and second layer of the outer cover structure, said adhesive being, in one exemplary embodiment of the invention, about 15 grams per square meter of the inner surface area of the outer cover structure. Using a controlled amount of adhesive has been found to be important in determining the optimal amount of water vapor and moisture transmission through the composite membrane of the outer cover structure and wicking layer and water vapor breathable layer. A minimal, controlled amount of thermoplastic polyester has been found to optimize the moisture vapor transfer rate as well as to enhance the wrinkling of the exterior surface of the water vapor breathable medium layer and the outer cover structure which is a visual indicator of water transmission functionality.

To provide additional strength and puncture protection to the outer cover structure 810 or 910, an additional outer layer of nylon mesh can be added. The nylon mesh can be, in one example or embodiment of the invention, a 15 denier monofilament nylon tricot with a basis weight (nominal) of 0.8 oz. per square yard. The nylon mesh can be a woven nylon mesh layer that is laminated together with the inner wicking and water vapor breathable layers. The lamination can be done using an adhesive, such as a trichloroethylene solvent based urethane adhesive. The adhesive can also be a thermoplastic polyester adhesive.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A water dissipation device for removing water vapor or moisture from a breathing circuit, comprising:
    an upper lid portion, an entry port for receiving flow from the breathing circuit, and an exit port for flow exiting the device;
    an outer cover structure extending from the upper lid portion to define an enclosed volume and having a depth between the upper lid portion and a bottom end portion of the device;
    an inner frame extending from the upper lid portion inside the outer cover structure, the device defining an inner flow space inside the enclosed volume at least for fluid flow from the entry port through the device to the exit port,
    said outer cover structure including at least a first layer of wicking material and a second layer of water vapor breathable medium over the first layer, the outer cover structure having an inner surface area bounding at least a portion of the inner flow space such that water vapor or moisture can permeate from the inner flow space through the outer cover structure out of device.

2. The water dissipation device of claim 1, further comprising:
    an inner cup structure extending from the upper lid portion into the enclosed volume, said inner cup structure being enclosed by the inner frame and defining and bounding at least a portion of the inner flow space.

3. The water dissipation device of claim 2,
    wherein the inner cup structure extends into the enclosed volume to displace a displacement volume inside the enclosed volume to define a compressible volume within the inner flow space inside the device.

4. The water dissipation device of claim 3,
    wherein the inner cup structure extends for a span of at least half the depth into the enclosed volume.

5. The water dissipation device of claim 2,
    wherein the inner flow space inside the enclosed volume defines a compressible volume inside the device, and the inner cup structure extends into the enclosed volume such that the compressible volume is less than approximately 67% of the enclosed volume.

6. The water dissipation device of claim 5,
    wherein the compressible volume is less than approximately 50% of the enclosed volume.

7. The water dissipation device of claim 2,
    wherein the inner cup structure includes a sidewall providing a visual water level indicator.

8. The water dissipation device of claim 7, wherein the visual water level indicator is provided by the sidewall having a first upper portion having a lower end and a second lower portion having an upper end, the lower end of the upper portion having a first width and the upper end of the lower portion having a second width different from the first width.

9. The water dissipation device of claim 2,
    wherein the inner cup structure has a non-circular cross-sectional shape transverse to the depth.

10. The water dissipation device of claim 1, further comprising:
    an array of flow vents disposed along an outer circumference of the device proximate the upper lid portion defining a plurality of flow paths from the entry port to the inner flow space.

11. The water dissipation device of claim 1, further comprising:
    a nylon mesh layer in the outer cover structure.

12. The water dissipation device of claim 11,
    wherein the first and second layer of the outer cover structure and the nylon mesh layer form a single composite laminate material.

13. The water dissipation device of claim 1, further comprising:
    a thermoplastic polyester adhesive bonding at least the first layer and second layer of the outer cover structure, said adhesive being about 15 grams per square meter of the inner surface area of the outer cover structure.

14. The water dissipation device of claim 1,
    wherein a ratio of the inner surface area of the outer cover structure over the depth is in the range of 10 to 12.5.

15. The water dissipation device of claim 1,
    wherein the device defines a cross-sectional shape transverse to the depth that is elliptical and non-circular.

16. A water dissipation device for removing water vapor or moisture from a breathing circuit, comprising:
- an upper lid portion, an entry port for receiving flow from the breathing circuit, and an exit port for flow exiting the device;
- an outer cover structure extending from the upper lid portion to define an enclosed volume and having a depth between the upper lid portion and a bottom end portion of the device;
- an inner frame extending from the upper lid portion inside the outer cover structure, the device defining an inner flow space inside the enclosed volume at least for fluid flow from the entry point through the device to the exit port, the inner frame including a substantially cylindrical annular wall portion extending from the upper lid portion for at least one half of the depth,
- said outer cover structure including at least a first layer of wicking material and a second layer of water vapor breathable medium over the first layer, the outer cover structure having an inner surface area bounding at least a portion of the inner flow space such that water vapor or moisture can permeate from the inner flow space through the outer cover structure out of device, the outer cover structure narrowly surrounding the annular wall portion of the inner frame to define a narrow annular flow space therebetween, the annular flow space being a portion of the inner flow space and in fluid communication with the entry port.

17. A water dissipation device of claim 16,
the inner frame further defining a return flow path inside the inner flow space and at least partially surrounded by the annular wall portion, said return flow path providing a flow pathway between the annular flow space and the exit port.

18. The water dissipation device of claim 17, further comprising:
a lower frame portion of the inner frame extending below the annular wall portion, the outer cover structure covering the lower frame portion to define a closed bottom end of the device, the lower frame portion defining at least one opening though which fluid may flow from the annular flow space to the return flow path.

19. The water dissipation device of claim 18, wherein the lower frame portion is a caged structure defining a plurality of windows being the at least one opening each permitting flow from the annular flow space to the return flow path.

20. The water dissipation device of claim 19,
wherein said plurality of windows extend from the closed bottom end of the device up to about one third of the depth.

21. The water dissipation device of claim 16,
wherein the annular wall portion of the inner frame defines at least one safety opening proximate the upper lid portion, providing a flow path from the annular flow space to the exit port.

22. The water dissipation device of claim 21,
wherein the at least one safety opening includes two safety openings having a combined area equal to an area of the entry port through which flow enters from the breathing circuit.

23. The water dissipation device of claim 16, further comprising:
an inner cup structure extending from the upper lid into the enclosed volume, said inner cup structure being enclosed by the inner frame and defining and bounding at least a portion of the inner flow space.

24. The water dissipation device of claim 23,
wherein the inner cup structure extends into the enclosed volume to displace a displacement volume inside the enclosed volume to define a compressible volume within the inner flow space inside the device.

25. The water dissipation device of claim 24,
wherein the inner cup structure extends for a span of at least half the depth into the enclosed volume.

26. The water dissipation device of claim 23,
wherein the inner flow space inside the enclosed volume defines a compressible volume inside the device, and the inner cup structure extends into the enclosed volume such that the compressible volume is less than approximately 67% of the enclosed volume.

27. The water dissipation device of claim 23,
wherein the inner cup structure includes a sidewall providing a visual water level indicator.

28. The water dissipation device of claim 27, wherein the visual water level indicator is provided by the sidewall having a first upper portion having a lower end and a second lower portion having an upper end, the lower end of the upper portion having a first width and the upper end of the lower portion having a second width different from the first width.

29. The water dissipation device of claim 23,
wherein the inner cup structure has a non-circular cross-sectional shape transverse to the depth.

30. The water dissipation device of claim 16, further comprising:
an array of flow vents disposed along an outer circumference of the device proximate the upper lid portion defining a plurality of flow paths from the entry port to the annular flow space.

31. The water dissipation device of claim 16, further comprising:
a nylon mesh layer in the outer cover structure.

32. The water dissipation device of claim 31,
wherein the first and second layer of the outer cover structure and the nylon mesh layer form a single composite laminate material.

33. The water dissipation device of claim 16, further comprising:
a thermoplastic polyester adhesive bonding at least the first layer and second layer of the outer cover structure, said adhesive being about 15 grams per square meter of the inner surface area of the outer cover structure.

34. The water dissipation device of claim 16,
wherein a ratio of the inner surface area of the outer cover structure over the depth is in the range of 11 to 14.

35. The water dissipation device of claim 16,
wherein the device defines a cross-sectional shape transverse to the depth that is elliptical and non-circular.

* * * * *